US007491835B2

(12) United States Patent
Donevan et al.

(10) Patent No.: US 7,491,835 B2
(45) Date of Patent: Feb. 17, 2009

(54) PRODRUGS OF AMINO ACIDS WITH AFFINITY FOR THE α2δ-PROTEIN

(75) Inventors: Sean D. Donevan, Dexter, MI (US); Augustine Tobi Osuma, Canton, MI (US); Andrew J. Thorpe, Whitmore Lake, MI (US); David Juergen Wustrow, Ann Arbor, MI (US)

(73) Assignee: Pfizer Inc, New York, NY (US)

( * ) Notice: Subject to any disclaimer, the term of this patent is extended or adjusted under 35 U.S.C. 154(b) by 424 days.

(21) Appl. No.: 10/946,540

(22) Filed: Sep. 21, 2004

(65) Prior Publication Data

US 2005/0070483 A1 Mar. 31, 2005

Related U.S. Application Data

(60) Provisional application No. 60/506,004, filed on Sep. 25, 2003.

(51) Int. Cl.
*C07C 233/00* (2006.01)
(52) U.S. Cl. ....................................... 554/63
(58) Field of Classification Search ........................ None
See application file for complete search history.

(56) References Cited

U.S. PATENT DOCUMENTS

| | | | |
|---|---|---|---|
| 5,344,957 | A | 9/1994 | Bovy et al. |
| 5,614,498 | A | 3/1997 | Ishikawa et al. |
| 5,840,961 | A | 11/1998 | Behling et al. |
| 6,011,066 | A | 1/2000 | Wang |
| 6,121,325 | A | 9/2000 | Chen et al. |
| 6,306,909 | B1 | 10/2001 | Weaver et al. |

FOREIGN PATENT DOCUMENTS

| | | |
|---|---|---|
| EP | 0 561 758 A2 | 9/1993 |
| EP | 0 561 758 A3 | 9/1993 |
| EP | 0 678 788 A2 | 10/1995 |
| EP | 0 678 788 A3 | 10/1995 |
| EP | 1 013 769 A1 | 6/2000 |
| FR | 1 377 736 A | 12/1963 |
| GB | 2 323 594 A | 9/1998 |
| WO | WO 91/09840 A1 | 7/1991 |
| WO | WO 95/15684 A1 | 6/1995 |
| WO | WO 98/17627 A1 | 4/1998 |
| WO | WO 98/40055 A2 | 9/1998 |
| WO | WO 98/40055 A3 | 9/1998 |
| WO | WO 98/56234 A1 | 12/1998 |
| WO | WO 00/76958 A2 | 12/2000 |
| WO | WO 00/76958 A3 | 12/2000 |
| WO | WO 01/87821 A1 | 11/2001 |
| WO | WO 01/88101 A2 | 11/2001 |
| WO | WO 01/88101 A3 | 11/2001 |
| WO | WO 02/22568 A1 | 3/2002 |
| WO | WO 02/30871 A1 | 4/2002 |
| WO | 02100344 | * 12/2002 |
| WO | WO 02/100344 A2 | 12/2002 |
| WO | WO 02/100344 A3 | 12/2002 |

OTHER PUBLICATIONS

Arvanitis, E., et al., "Enantioselective synthesis of 2-substituted 3-amniopropanoic acid (Beta-alanine) derivatives which are Beta-analogues of aromatic amino acids". J. Chem. Soc., Perkin Trans. 1. 1998. pp. 521-528.

Baskakov. Y. A. et al., "Preparation of the Cyclic Hydrazide of Maleic Acid and of Some of its Derivatives", Database Crossfire Beilstein, Beilstein Institut Zur Foerderung Der Chenischen Wissenschaften, Frankfurt Am Main. DE Database Accession No. 1770439 (BRN), XP002242312 & Zh. Obshch. Khim., 1954, vol. 24, pp. 1205-1208.

Borodina, G.M., et al., "Synthesis of Some Derivatives of Aliphatic Beta-Amino Acids". Chemical Abstracts. 1955. vol. 49. No. 18, col. 1, pp. 12291, (Abstract Only).

Bull, S.D. et al., "Asymmetric synthesis of Beta-amino acid scaffolds", J. Chem. Soc. Perkin Trans 1, 2001 vol. 22. pp. 2931-2938.

Database Crossfire Beilstein. Beilstein Institut Zur Foerderung Der Chenischen Wissenchaften. Frankfurt Am Main, DE Database Accession No. 1723420 (BRN). XP002242310 & Zh. Obshch. Khim., 1956. vol. 26. pp. 793-796.

Davies, S. G. et al. "Asymmetric Syntheses of Beta-Phenylalanine, Alpha-Methyl-Beta-Phenylalanines and Derivatives". J. Chem. Soc., Chem. Commun., 1993. pp. 1153-1155.

Davies, S. G., et al. "A Succinct Asymmetric Synthesis of (2S,3R)-2-Methyl-3-aminopentanoic Acid Hydrochloride". Synlett. 1994. pp. 117-118.

Davis, F.A., et al., "Concise Asymmetric Synthesis of Alpha-Amino Acid Derivatives from N-Sulfinylimino Esters." J. Org. Chem., 1999. vol. 64 pp. 3396-3397.

Davis, F.A. et al., "Improved Synthesis of Enantiopure Sulfinimines (Thiooxime S-Oxides) from p-Toluenesulfinamide and Aldehydes and Ketones," J. Org. Chem. 1999, vol. 64, pp. 1403-1406.

Dixon, W. J., W., "Efficient Analysis of Experimental Observations". Ann. Rev. Pharmacol. Toxicol., 1980, vol. 20, pp. 441-462.

Evans, D. A. et al. "A General Method for the Synthesis of Enantiomerically Pure Beta-Substituted, Beta-Amino Acids through Alpha-Substituted Succinic Acid Derivatives", J. Org. Chem., 1999, vol. 64. pp. 6411-6417.

Gallop. Mark, et al., "Amino acid conjugates providing for sustained systemic concentrations of GABA analogs", Database CA Online! Chemical Abstracts Service, XP002319859.

Gee. N. S. et al, "The Novel Anticonvulsant Drug. Gabapentin (Neurontin), Binds to the Alpha2Beta Subunit of a Calcium Channel". J. Biol. Chem., 1996. vol. 271, No. 10, pp. 5768-5776.

(Continued)

*Primary Examiner*—Deborah D Carr
(74) *Attorney, Agent, or Firm*—Steve T. Zelson; Garth Butterfield; Patricia K. Fitzsimmons

(57) ABSTRACT

This invention relates to prodrugs of certain amino acids that bind to the alpha-2-delta (α2δ) subunit of a calcium channel. These compounds and their pharmaceutically acceptable salts are useful in the treatment of a variety of psychiatric, pain and other disorders.

12 Claims, No Drawings

OTHER PUBLICATIONS

Gerwick, W. et al., "Total Structure of Hormothamnin A, A Toxic Cyclic Undecapeptide From the Tropical Marine Cyanobacterium Hormothamnion Enteromorphoides". Tetrahedron, 1992, vol. 48, No. 12. pp. 2313-2324.

Gol'dfarb, Y.L. et al., "Synthesis of Aliphatic Amino Acids from Thiophene Derivatives", Chemical Abstracts, vol. 8, col. 2, p. 12837 (Abstract Only).

Griffith. O.W. et al., "Liquid Chromatographic Separation of Enantiomers of Beta-Amino Acids Using a Chiral Stationary Phase". Chemical Abstract, 1986, vol. 105, No. 21, (Abstract Only).

Hargreaves. K. et al, "A New and Sensitive Method for Measuring Thermal Nociception in Cutaneous Hyperalgesia". Pain, 1988, vol. 32, pp. 77-88.

Hawkins J. et al., "Asymmetric Michael Reactions of 3,5-Dihydro-4H-dinaphth[2,1-c:1'.2'-e]azepine with Methyl Crotonate", J.Org. Chem., 1986, vol. 51, pp. 2820-2822.

Hill. R. K. et al., "Asymmetric Induction in the Thermal Reactions of Allylic Alcohols with N. N-Dimethylacetamide Dimethyl Acetal and Triethyl Orthoacetate". J. Oor. Chem.. 1972. vol. 37. No. 23, pp. 3737-3740.

Hintermann T. et al., "A Useful Modification of the Evans Auxilliary: 4-Isopropyl-5,5-diphenyloxazolidin-2-one," Helvetica Chimica Acta. 1998. vol. 81. pp. 2093-2126.

Ho, G.J. et al. "Lithium-Initiated Imide Formation. A Siimple Method for N-Acylation of 2-Oxazolidinones and Bornane-2, 10-Sultam", J. Org. Chem., 1995, vol. 60, pp. 2271-2273.

Ishikawa et al, "Chiral Lewis Acid-Hydroxylamine Hybrid Reagent for Enantioselective Michael Addition Reaction Directed Towards Beta-Amino Acids Synthesis", SYNLETT, 1998, vol. 11, pp. 1291-1293.

Jefford, C. et al., "An Enantiospecific Synthesis of Beta-Amino Acids", Tetrahedron Letters. 1993. vol. 34, No. 7. pp. 1111-1114.

Juraristi. E. et al., "Enantioselective Synthesis of Beta-Amino Acids. 7. Preparation of Enantiopure Amino-Substituted Beta-Amino Acids from 1-Benzoyl-2(S)-tert-butyl-3-methylperhydropyrimidin-4-one. 1,2", Tetrahedron, 1996, vol. 7, No. 8, pp. 2233-2246.

Lazar. L., et al., "A Simple Synthesis of Beta-Alkyl-Substituted Beta-Amino Acids". Synth. Commun., 1998, vol. 28(2). pp. 219-224.

Liang, J. et al, "Synthesis of Unit A of Cryptophycin via a [2,3]-Wittig Rearrangement", J. Org. Chem., 1999, vol. 64, pp. 1459-1463.

Myers. A. G. et al., "Highly Practical Methodology for the Synthesis of D- and L-Alpha-Amino Acids, N-Protected Alpha-Amino Acids, and N-Methyl-Alpha-Amino Acids." J. Am. Chem. Soc., 1997, vol. 119, pp. 656-673.

Nagula, G. et al., "Synthesis of Alpha-Substituted Beta-Amino Acids Using Pseudoephedrine as a Chiral Auxiliary," Org. Letters, 2000, vol. 2, pp. 3527-3529.

Paine III, J.B. et al. "Pyrrole Chemistry. The Cyanovinyl Aldehyde Protecting Groups", J. Org. Chem., 1976. vol. 41. No. 17, pp. 2826-2835.

Palomino E., "Delivery of Drugs Through Dihydropyridine Carriers". Drugs of the Future. 1990. vol. 15, No. 4. pp. 361-368.

Randall L.O., et al. "A Method for Measurement of Analgesic Activitity On Inflamed Tissue", Arch. Int. Pharmacodyn., 1957, vol. 4, pp. 409-419.

Rodionov, V. M., et al. "Synthesis and Separation of Diastereoisomeric Gamma-Ethyl-Beta-Aminocaprylic Acids and Their Derivatives". Chemical Abstracts, 1956, vol. 50, No. 20 (Abstract Only).

Rodionov. V.M., et al., "The Hoffmann reaction. III. Reaction of Acylated Amides of Beta-Aminopelagonic Acid with Alkaline Hypobromites", Chemical Abstracts, 1951, col. 1, vol. 45, No. 19, pp. 8453.

Seebach, D. et al. "EPC-Synthesis of Beta-Amino Acid Derivatives through Lithiated Hydropyrimidines" Eur. J. Org. Chem., 1999. pp. 335-360.

Sibi, M.P. et al., "A New Methodology for the Synthesis of Beta-Amino Acids". J. Chem. Soc., Perkin Trans.1. 2000, vol. 9, pp. 1461-1466.

Slopianka. M. et al., "Thiocaronyl Olefination", Chemical Abstracts. 1981. vol. 96. No. 13 (Abstract Only).

Sluka, K., et al, "Unilateral Intramuscular Injections of Acidic Saline Produce a Bilateral, Long-Lasting Hyperalgesia". Muscle Nerve. 2001. vol. 24. pp. 37-46.

Tang, T. P. et al, "The tert-Butanesulfinyl Group: An Ideal Chiral Directing Group and Boc-Surrogate for the Asymmetric Synthesis and Applications of Beta-Amino Acids", J. Org. Chem., 1999, vol. 64, pp. 12-13.

Vara Prasad. J. V. N., et al., "2,2'-Dithiobisbenzamides Derived from Alpha-, Beta- and Gamma-Amino Acids Possessing Anti-HIV Activities: Synthesis and Structure-Activity Relationship", Bioorganic & Medicinal Chemistry, 1998. pp. 1707-1730.

Vogel. J.R. et al, "A Simple and Reliable Conflict Procedure for Testing Anti-Anxiety Agents", Psychopharmacologia, 1971. vol. 21, pp. 1-7.

Yuen P. W. et al. "Enantioselective Synthesis of PD144723: A Potent Stereospecific Anticonvulsant", Bioorganic & Medicinal Chemistry Letters, 1994, vol. 4, No. 6. pp. 823-825.

Zimmerman, J., et al., "The Effect of Active Ester Components on Racemization in the Synthesis of Peptides by the Dicyclohexylcarbodimide Method", Journal of the American Chemical Society. Dec. 20, 1967. 89:26 pp. 7151-7152.

* cited by examiner

PRODRUGS OF AMINO ACIDS WITH AFFINITY FOR THE α2δ-PROTEIN

This application is a U.S. utility application, which claims the benefit of priority to U.S. Provisional Application No. 60/506,004, filed Sep. 25, 2003.

BACKGROUND OF THE INVENTION

This invention relates to certain compounds that bind to the alpha-2-delta (α2δ) subunit of a calcium channel. More specifically, the α2δ compounds of the present invention are prodrugs of the active α2δ compound.

The prodrugs of the present invention, that when administered to humans or other mammals, provide an increased duration of active compound in the plasma compared to compounds of the corresponding structure in which the labile groups are not present. Compounds of the present invention were expected to produce sustained levels of active compound in the plasma over time when compared to the parent structures. One advantage of the prodrugs over the parent structure is that the prodrugs are absorbed by active processes other than those involved in the active absorption of the parent structures. This may lead to absorption over greater lengths of the gastrointestinal tract when compared to the parent structures. An advantage of the present invention is to promote sustained absorption of the prodrugs.

SUMMARY OF THE INVENTION

This invention relates to compounds of the formula I and the pharmaceutically acceptable salts of such compounds.

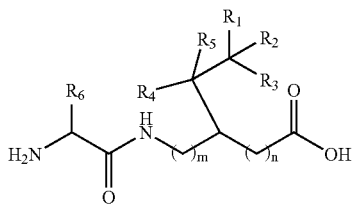

I wherein $R_1$ is hydrogen or $(C_1-C_{10})$alkyl optionally substituted with from one to five fluorine atoms;

$R_2$ is hydrogen or $(C_1-C_6)$alkyl;

$R_1$ and $R_2$, together with the carbon to which they are attached, may form a three to six membered cycloalkyl ring;

$R_3$ is hydrogen or $(C_1-C_8)$alkyl, $(C_3-C_6)$cycloalkyl, $(C_3-C_6)$cycloalkyl-$(C_1-C_6)$alkyl, phenyl, phenyl-$(C_1-C_3)$alkyl, pyridyl, pyridyl-$(C_1-C_3)$alkyl, wherein each of the foregoing alkyl moieties can be optionally substituted with from one to five fluorine atoms, preferably with from zero to three fluorine atoms, and wherein said phenyl and said pyridyl and the phenyl and pyridyl moieties of said phenyl-$(C_1-C_3)$alkyl and said pyridyl-$(C_1-C_3)$alkyl, respectively, can be optionally substituted with from one to three substituents, preferably with from zero to two substituents, independently selected from chloro, fluoro, amino, nitro, cyano, $(C_1-C_3)$alkylamino, $(C_1-C_3)$alkyl optionally substituted with from one to three fluorine atoms and $(C_1-C_3)$alkoxy optionally substituted with from one to three fluorine atoms;

$R_4$ is hydrogen or $(C_1-C_6)$alkyl optionally substituted with from one to five fluorine atoms;

$R_5$ is hydrogen or $(C_1-C_6)$alkyl optionally substituted with from one to five fluorine atoms;

$R_4$ and $R_5$, together with the carbon to which they are attached, may form a three to six membered cycloalkyl ring;

$R_6$ is a side chain derived from a naturally occurring α-amino endogenous amino acid or other $(C_1-C_8)$alkyl;

m=0 or 1;

n=0 or 1; and m and n cannot both be 0 at the same time.

Specific embodiments of this invention include the following compounds of the formula I and their pharmaceutically acceptable salts:

3-[(2-Amino-4-methyl-pentanoylamino)-methyl]-5-methyl-octanoic acid;

3-[(2-Amino-4-methyl-pentanoylamino)-methyl]-5-methyl-heptanoic acid;

3-[(2-Amino-4-methyl-pentanoylamino)-methyl]-5-methyl-nonanoic acid;

3-[(2-Amino-4-methyl-pentanoylaniino)-methyl]-4,5-dimethyl-heptanoic acid;

3-[(2-Amino-4-methyl-pentanoylamino)-methyl]-4,5-dimethyl-octanoic acid;

3-[(2-Amino-4-methyl-pentanoylamino)-methyl]-4,5-dimethyl-nonanoic acid;

3-[(2-Amino-4-methyl-pentanoylamino)-methyl]-5-methyl-hexanoic acid;

3-[(2-Amino-4-methyl-pentanoylamino)-methyl]-4,5-dimethyl-hexanoic acid;

3-[(2-Amino-3-methyl-pentanoylamino)-methyl]-5-methyl-heptanoic acid;

3-[(2-Amino-3-methyl-pentanoylamino)-methyl]-5-methyl-octanoic acid;

3-[(2-Amino-3-methyl-pentanoylamino)-methyl]-5-methyl-nonanoic acid;

3-[(2-Amino-3-methyl-pentanoylamino)-methyl]-4,5-dimethyl-heptanoic acid;

3-[(2-Amino-3-methyl-pentanoylamino)-methyl]-4,5-dimethyl-octanoic acid;

3-[(2-Amino-3-methyl-pentanoylamino)-methyl]-4,5-dimethyl-nonanoic acid;

3-[(2-Amino-3-methyl-pentanoylaniino)-methyl]-5-methyl-hexanoic acid;

3-[(2-Amino-3-methyl-pentanoylamino)-methyl]-4,5-dimethyl-hexanoic acid;

3-[(2-Amino-3-methyl-butyrylamino)-methyl]-5-methyl-heptanoic acid;

3-[(2-Amino-3-methyl-butyrylamino)-methyl]-5-methyl-octanoic acid;

3-[(2-Amino-3-methyl-butyrylamino)-methyl]-5-methyl-nonanoic acid;

3-[(2-Amino-3-methyl-butyrylamino)-methyl]-4,5-dimethyl-heptanoic acid;

3-[(2-Amino-3-methyl-butyrylamino)-methyl]-4,5-dimethyl-octanoic acid;

3-[(2-Amino-3-methyl-butyrylamino)-methyl]-4,5-dimethyl-nonanoic acid;

3-[(2-Amino-3-methyl-butyrylamino)-methyl]-5-methyl-hexanoic acid;

3-[(2-Amino-3-methyl-butyrylamino)-methyl]-4,5-dimethyl-hexanoic acid;

3-[(2-Amino-propionylamino)-methyl]-5-methyl-heptanoic acid;

3-[(2-Amino-propionylamino)-methyl]-5-methyl-octanoic acid;

3-[(2-Amino-propionylamino)-methyl]-5-methyl-nonanoic acid;

3-[(2-Amino-propionylamino)-methyl]-4,5-dimethyl-heptanoic acid;

3-[(2-Amino-propionylamino)-methyl]-4,5-dimethyl-octanoic acid;
3-[(2-Amino-propionylamino)-methyl]-4,5-dimethyl-nonanoic acid;
3-[(2-Amino-propionylamino)-methyl]-5-methyl-hexanoic acid;
3-[(2-Amino-propionylamino)-methyl]-4,5-dimethyl-hexanoic acid;
3-[(2-Amino-acetylamino)-methyl]-5-methyl-heptanoic acid;
3-[(2-Amino-acetylamino)-methyl]-5-methyl-octanoic acid;
3-[(2-Amino-acetylamino)-methyl]-5-methyl-heptanoic acid;
3-[(2-Amino-acetylamino)-methyl]-4,5-dimethyl-heptanoic acid;
3-[(2-Amino-acetylamino)-methyl]-4,5-dimethyl-octanoic acid;
3-[(2-Amino-acetylamino)-methyl]-4,5-dimethyl-nonanoic acid;
3-[(2-Amino-acetylamino)-methyl]-5-methyl-hexanoic acid;
3-[(2-Amino-acetylamino)-methyl]-4,5-dimethyl-hexanoic acid;
3-(2-Amino-acetylamino)-5-methyl-heptanoic acid;
3-(2-Amino-acetylamino)-5-methyl-octanoic acid;
3-(2-Amino-acetylamino)-5-methyl-nonanoic acid;
3-(2-Amino-acetylamino)-4,5-dimethyl-heptanoic acid;
3-(2-Amino-acetylamino)-4,5-dimethyl-octanoic acid;
3-(2-Amino-acetylamino)-4,5-dimethyl-nonanoic acid;
3-(2-Amino-propionylamino)-5-methyl-heptanoic acid;
3-(2-Amino-propionylamino)-5-methyl-octanoic acid;
3-(2-Amino-propionylamino)-5-methyl-nonanoic acid;
3-(2-Amino-propionylamino)-4,5-dimethyl-heptanoic acid;
3-(2-Amino-propionylamino)-4,5-dimethyl-octanoic acid;
3-(2-Amino-propionylamino)-4,5-dimethyl-nonanoic acid;
3-(2-Amino-3-methyl-butyrylamino)-5-methyl-heptanoic acid;
3-(2-Amino-3-methyl-butyrylamino)-5-methyl-octanoic acid;
3-(2-Amino-3-methyl-butyrylamino)-5-methyl-nonanoic acid;
3-(2-Amino-3-methyl-butyrylamino)-4,5-dimethyl-heptanoic acid;
3-(2-Amino-3-methyl-butyrylamino)-4,5-dimethyl-octanoic acid;
3-(2-Amino-3-methyl-butyrylamino)-4,5-dimethyl-nonanoic acid;
3-(2-Amino-3-methyl-pentanoylamino)-5-methyl-heptanoic acid;
3-(2-Amino-3-methyl-pentanoylamino)-5-methyl-octanoic acid;
3-(2-Amino-3-methyl-pentanoylamino)-5-methyl-nonanoic acid;
3-(2-Amino-3-methyl-pentanoylamino)-4,5-dimethyl-heptanoic acid;
3-(2-Amino-3-methyl-pentanoylamino)-4,5-dimethyl-octanoic acid;
3-(2-Amino-3-methyl-pentanoylamino)-4,5-dimethyl-nonanoic acid;
3-(2-Amino-4-methyl-pentanoylamino)-5-methyl-heptanoic acid;
3-(2-Amino-4-methyl-pentanoylamino)-5-methyl-octanoic acid;
3-(2-Amino-4-methyl-pentanoylamino)-5-methyl-nonanoic acid;
3-(2-Amino4-methyl-pentanoylamino)-4,5-dimethyl-heptanoic acid;
3-(2-Amino-4-methyl-pentanoylamino)-4,5-dimethyl-octanoic acid; and
3-(2-Amino4-methyl-pentanoylamino)-4,5-dimethyl-nonanoic acid.

More preferred are compounds of formula II

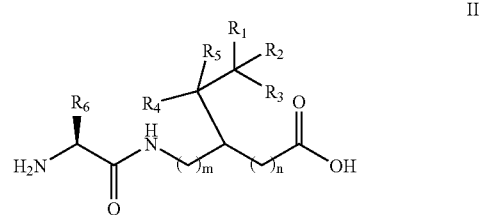

wherein, $R_1$, $R_2$, $R_3$, $R_4$, $R_5$, and $R_6$, m and n, are defined as above and wherein said compounds are selected from the following compounds and their pharmaceutically acceptable salts:

3-[(2S-Amino4-methyl-pentanoylamino)-methyl]-5-methyl-octanoic acid;
3-[(2S-Amino-4-methyl-pentanoylamino)-methyl]-5-methyl-heptanoic acid;
3-[(2S-Amino-4-methyl-pentanoylamino)-methyl]-5-methyl-nonanoic acid;
3-[(2S-Amino-4-methyl-pentanoylamino)-methyl]-4,5-dimethyl-heptanoic acid;
3-[(2S-Amino-4-methyl-pentanoylamino)-methyl]-4,5-dimethyl-octanoic acid;
3-[(2S-Amino-4-methyl-pentanoylamino)-methyl]-4,5-dimethyl-nonanoic acid;
3-[(2S-Amino-4-methyl-pentanoylamino)-methyl]-5-methyl-hexanoic acid;
3-[(2S-Amino-4-methyl-pentanoylamino)-methyl]-4,5-dimethyl-hexanoic acid;
3-[(2S-Amino-3-methyl-pentanoylamino)-methyl]-5-methyl-heptanoic acid;
3-[(2S-Amino-3-methyl-pentanoylamino)-methyl]-5-methyl-octanoic acid;
3-[(2S-Amino-3-methyl-pentanoylamino)-methyl]-5-methyl-nonanoic acid;
3-[(2S-Amino-3-methyl-pentanoylamino)-methyl]-4,5-dimethyl-heptanoic acid;
3-[(2S-Amino-3-methyl-pentanoylamino)-methyl]-4,5-dimethyl-octanoic acid;
3-[(2S-Amino-3-methyl-pentanoylamino)-methyl]4,5-dimethyl-nonanoic acid;
3-[(2S-Amino-3-methyl-pentanoylamino)-methyl]-5-methyl-hexanoic acid;
3-[(2S-Amino-3-methyl-pentanoylamino)-methyl]-4,5-dimethyl-hexanoic acid;
3-[(2S-Amino-3-methyl-butyrylamino)-methyl]-5-methyl-heptanoic acid;
3-[(2S-Amino-3-methyl-butyrylamino)-methyl]-5-methyl-octanoic acid;
3-[(2S-Amino-3-methyl-butyrylamino)-methyl]-5-methyl-nonanoic acid;
3-[(2S-Amino-3-methyl-butyrylamino)-methyl]-4,5-dimethyl-heptanoic acid;
3-[(2S-Amino-3-methyl-butyrylamino)-methyl]-4,5-dimethyl-octanoic acid;
3-[(2S-Amino-3-methyl-butyrylamino)-methyl]-4,5-dimethyl-nonanoic acid;

3-[(2S-Amino-3-methyl-butyrylamino)-methyl]-5-methyl-hexanoic acid;
3-[(2S-Amino-3-methyl-butyrylamino)-methyl]-4,5-dimethyl-hexanoic acid;
3-[(2S-Amino-propionylamino)-methyl]-5-methyl-heptanoic acid;
3-[(2S-Amino-propionylamino)-methyl]-5-methyl-octanoic acid;
3-[(2S-Amino-propionylamino)-methyl]-5-methyl-nonanoic acid;
3-[(2S-Amino-propionylamino)-methyl]-4,5-dimethyl-heptanoic acid;
3-[(2S-Amino-propionylamino)-methyl]-4,5-dimethyl-octanoic acid;
3-[(2S-Amino-propionylamino)-methyl]-4,5-dimethyl-nonanoic acid;
3-[(2S-Amino-propionylamino)-methyl]-5-methyl-hexanoic acid;
3-[(2S-Amino-propionylamino)-methyl]-4,5-dimethyl-hexanoic acid;
3-[(2S-Amino-acetylamino)-methyl]-5-methyl-heptanoic acid;
3-[(2S-Amino-acetylamino)-methyl]-5-methyl-octanoic acid;
3-[(2S-Amino-acetylamino)-methyl]-5-methyl-heptanoic acid;
3-[(2S-Amino-acetylamino)-methyl]-4,5-dimethyl-heptanoic acid;
3-[(2S-Amino-acetylamino)-methyl]-4,5-dimethyl-octanoic acid;
3-[(2S-Amino-acetylamino)-methyl]-4,5-dimethyl-nonanoic acid;
3-[(2S-Amino-acetylamino)-methyl]-5-methyl-hexanoic acid;
3-[(2S-Amino-acetylamino)-methyl]-4,5-dimethyl-hexanoic acid;
3-(2S-Amino-acetylamino)-5-methyl-heptanoic acid;
3-(2S-Amino-acetylamino)-5-methyl-octanoic acid;
3-(2S-Amino-acetylamino)-5-methyl-nonanoic acid;
3-(2S-Amino-acetylamino)4,5-dimethyl-heptanoic acid;
3-(2S-Amino-acetylamino)4,5-dimethyl-octanoic acid;
3-(2S-Amino-acetylamino)4,5-dimethyl-nonanoic acid;
3-(2S-Amino-propionylamino)-5-methyl-heptanoic acid;
3-(2S-Amino-propionylamino)-5-methyl-octanoic acid;
3-(2S-Amino-propionylamino)-5-methyl-nonanoic acid;
3-(2S-Amino-propionylamino)-4,5-dimethyl-heptanoic acid;
3-(2S-Amino-propionylamino)-4,5-dimethyl-octanoic acid;
3-(2S-Amino-propionylamino)-4,5-dimethyl-nonanoic acid;
3-(2S-Amino-3-methyl-butyrylamino)-5-methyl-heptanoic acid;
3-(2S-Amino-3-methyl-butyrylamino)-5-methyl-octanoic acid;
3-(2S-Amino-3-methyl-butyrylamino)-5-methyl-nonanoic acid;
3-(2S-Amino-3-methyl-butyrylamino)-4,5-dimethyl-heptanoic acid;
3-(2S-Amino-3-methyl-butyrylamino)-4,5-dimethyl-octanoic acid;
3-(2S-Amino-3-methyl-butyrylamino)-4,5-dimethyl-nonanoic acid;
3-(2S-Amino-3-methyl-pentanoylamino)-5-methyl-heptanoic acid;
3-(2S-Amino-3-methyl-pentanoylamino)-5-methyl-octanoic acid;
3-(2S-Amino-3-methyl-pentanoylamino)-5-methyl-nonanoic acid;
3-(2S-Amino-3-methyl-pentanoylamino)-4,5-dimethyl-heptanoic acid;
3-(2S-Amino-3-methyl-pentanoylamino)-4,5-dimethyl-octanoic acid;
3-(2S-Amino-3-methyl-pentanoylamino)-4,5-dimethyl-nonanoic acid;
3-(2S-Amino-4-methyl-pentanoylamino)-5-methyl-heptanoic acid;
3-(2S-Amino-4-methyl-pentanoylamino)-5-methyl-octanoic acid;
3-(2S-Amino-4-methyl-pentanoylamino)-5-methyl-nonanoic acid;
3-(2S-Amino-4-methyl-pentanoylamino)-4,5-dimethyl-heptanoic acid;
3-(2S-Amino-4-methyl-pentanoylamino)-4,5-dimethyl-octanoic acid; and
3-(2S-Amino-4-methyl-pentanoylamino)-4,5-dimethyl-nonanoic acid.

Even more preferred are compounds of formula III

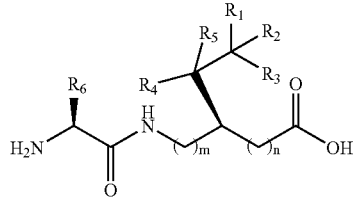

wherein, $R_1$, $R_2$, $R_3$, $R_4$, $R_5$, $R_6$, m and n are defined as above and wherein said compounds are selected from the following compounds and their pharmaceutically acceptable salts:

3S-[(2S-Amino-4-methyl-pentanoylamino)-methyl]-5R-methyl-octanoic acid;
3S-[(2S-Amino-4-methyl-pentanoylamino)-methyl]-5R-methyl-heptanoic acid;
3S-[(2S-Amino-4-methyl-pentanoylamino)-methyl]-5R-methyl-nonanoic acid;
3R-[(2S-Amino-4-methyl-pentanoylamino)-methyl]-4R,5R-dimethyl-heptanoic acid;
3R-[(2S-Amino-4-methyl-pentanoylamino)-methyl]-4R,5R-dimethyl-octanoic acid;
3R-[(2S-Amino-4-methyl-pentanoylamino)-methyl]-4R,5R-dimethyl-nonanoic acid;
3S-[(2S-Amino-4-methyl-pentanoylamino)-methyl]-5R-methyl-hexanoic acid;
3R-[(2S-Amino-4-methyl-pentanoylamino)-methyl]-4R,5R-dimethyl-hexanoic acid;
3S-[(2S-Amino-3-methyl-pentanoylamino)-methyl]-5R-methyl-heptanoic acid;
3S-[(2S-Amino-3-methyl-pentanoylamino)-methyl]-5R-methyl-octanoic acid;
3S-[(2S-Amino-3-methyl-pentanoylamino)-methyl]-5R-methyl-nonanoic acid;
3R-[(2S-Amino-3-methyl-pentanoylamino)-methyl]4R,5R-dimethyl-heptanoic acid;
3R-[(2S-Amino-3-methyl-pentanoylamino)-methyl]4R,5R-dimethyl-octanoic acid;
3R-[(2S-Amino-3-methyl-pentanoylamino)-methyl]4R,R5-dimethyl-nonanoic acid;
3S-[(2S-Amino-3-methyl-pentanoylamino)-methyl]-5R-methyl-hexanoic acid;
3R-[(2S-Amino-3-methyl-pentanoylamino)-methyl]-4R,5R-dimethyl-hexanoic acid;

3S-[(2S-Amino-3-methyl-butyrylamino)-methyl]-5R-methyl-heptanoic acid;
3S-[(2S-Amino-3-methyl-butyrylamino)-methyl]-5R-methyl-octanoic acid;
3S-[(2S-Amino-3-methyl-butyrylamino)-methyl]-5R-methyl-nonanoic acid;
3R-[(2S-Amino-3-methyl-butyrylamino)-methyl]-4R,5R-dimethyl-heptanoic acid;
3R-[(2S-Amino-3-methyl-butyrylamino)-methyl]-4R,5R-dimethyl-octanoic acid;
3R-[(2S-Amino-3-methyl-butyrylamino)-methyl]-4R,5R-dimethyl-nonanoic acid;
3S-[(2S-Amino-3-methyl-butyrylamino)-methyl]-5R-methyl-hexanoic acid;
3R-[(2S-Amino-3-methyl-butyrylamino)-methyl]-4R,5R-dimethyl-hexanoic acid;
3S-[(2S-Amino-propionylamino)-methyl]-5R-methyl-heptanoic acid;
3S-[(2S-Amino-propionylamino)-methyl]-5R-methyl-octanoic acid;
3S-[(2S-Amino-propionylamino)-methyl]-5R-methyl-nonanoic acid;
3R-[(2S-Amino-propionylamino)-methyl]-4R,5R-dimethyl-heptanoic acid;
3R-[(2S-Amino-propionylamino)-methyl]-4R,5R-dimethyl-octanoic acid;
3R-[(2S-Amino-propionylamino)-methyl]-4R,5R-dimethyl-nonanoic acid;
3S-[(2S-Amino-propionylamino)-methyl]-5R-methyl-hexanoic acid;
3R-[(2S-Amino-propionylamino)-methyl]-4R,5R-dimethyl-hexanoic acid;
3S-[(2S-Amino-acetylamino)-methyl]-5R-methyl-heptanoic acid;
3S-[(2S-Amino-acetylamino)-methyl]-5R-methyl-octanoic acid;
3S-[(2S-Amino-acetylamino)-methyl]-5R-methyl-heptanoic acid;
3R-[(2S-Amino-acetylamino)-methyl]-4R,5R-dimethyl-heptanoic acid;
3R-[(2S-Amino-acetylamino)-methyl]-4R,5R-dimethyl-octanoic acid;
3R-[(2S-Amino-acetylamino)-methyl]-4R,5R-dimethyl-nonanoic acid;
3S-[(2S-Amino-acetylamino)-methyl]-5R-methyl-hexanoic acid;
3R-[(2S-Amino-acetylamino)-methyl]-4R,5R-dimethyl-hexanoic acid;
3S-(2S-Amino-acetylamino)-5R-methyl-heptanoic acid;
3S-(2S-Amino-acetylamino)-5R-methyl-octanoic acid;
3S-(2S-Amino-acetylamino)-5R-methyl-nonanoic acid;
3R-(2S-Amino-acetylamino)-4R,5R-dimethyl-heptanoic acid;
3R-(2S-Amino-acetylamino)-4R,5R-dimethyl-octanoic acid;
3R-(2S-Amino-acetylamino)-4R,5R-dimethyl-nonanoic acid;
3R-(2S-Amino-propionylamino)-5R-methyl-heptanoic acid;
3S-(2S-Amino-propionylamino)-5R-methyl-octanoic acid;
3S-(2S-Amino-propionylamino)-5R-methyl-nonanoic acid;
3R-(2S-Amino-propionylamino)-4R,5R-dimethyl-heptanoic acid;
3R-(2S-Amino-propionylamino)-4R,5R-dimethyl-octanoic acid;
3R-(2S-Amino-propionylamino)-4R,5R-dimethyl-nonanoic acid;
3S-(2S-Amino-3-methyl-butyrylamino)-5R-methyl-heptanoic acid;
3S-(2S-Amino-3-methyl-butyrylamino)-5R-methyl-octanoic acid;
3S-(2S-Amino-3-methyl-butyrylamino)-5R-methyl-nonanoic acid;
3R-(2S-Amino-3-methyl-butyrylamino)-4R,5R-dimethyl-heptanoic acid;
3R-(2S-Amino-3-methyl-butyrylamino)-4R,5R-dimethyl-octanoic acid;
3R-(2S-Amino-3-methyl-butyrylamino)-4R,5R-dimethyl-nonanoic acid;
3S-(2S-Amino-3-methyl-pentanoylamino)-5R-methyl-heptanoic acid;
3S-(2S-Amino-3-methyl-pentanoylamino)-5R-methyl-octanoic acid;
3S-(2S-Amino-3-methyl-pentanoylamino)-5R-methyl-nonanoic acid;
3R-(2S-Amino-3-methyl-pentanoylamino)-4R,5R-dimethyl-heptanoic acid;
3R-(2S-Amino-3-methyl-pentanoylamino)-4R,5R-dimethyl-octanoic acid;
3R-(2S-Amino-3-methyl-pentanoylamino)-4R,5R-dimethyl-nonanoic acid;
3S-(2S-Amino-4-methyl-pentanoylamino)-5R-methyl-heptanoic acid;
3S-(2S-Amino-4-methyl-pentanoylamino)-5R-methyl-octanoic acid;
3S-(2S-Amino-4-methyl-pentanoylamino)-5R-methyl-nonanoic acid;
3R-(2S-Amino-4-methyl-pentanoylamino)-4R,5R-dimethyl-heptanoic acid;
3R-(2S-Amino-4-methyl-pentanoylamino)-4R,5R-dimethyl-octanoic acid; and
3R-(2S-Amino-4-methyl-pentanoylamino)-4R,5R-dimethyl-nonanoic acid.

Even more preferred are compounds of formula IV

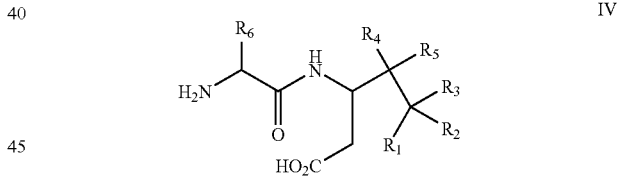

wherein, $R_1$, $R_2$, $R_3$, $R_4$, $R_5$, and $R_6$ are defined as above and wherein said compounds are selected from the following compounds and their pharmaceutically acceptable salts:
3-(2-Amino-acetylamino)-5-methyl-heptanoic acid;
3-(2-Amino-acetylamino)-5-methyl-octanoic acid;
3-(2-Amino-acetylamino)-5-methyl-nonanoic acid;
3-(2-Amino-acetylamino)-4,5-dimethyl-heptanoic acid;
3-(2-Amino-acetylamino)-4,5-dimethyl-octanoic acid;
3-(2-Amino-acetylamino)-4,5-dimethyl-nonanoic acid;
3-(2-Amino-propionylamino)-5-methyl-heptanoic acid;
3-(2-Amino-propionylamino)-5-methyl-octanoic acid;
3-(2-Amino-propionylamino)-5-methyl-nonanoic acid;
3-(2-Amino-propionylamino)-4,5-dimethyl-heptanoic acid;
3-(2-Amino-propionylamino)-4,5-dimethyl-octanoic acid;
3-(2-Amino-propionylamino)-4,5-dimethyl-nonanoic acid;
3-(2-Amino-3-methyl-butyrylamino)-5-methyl-heptanoic acid;
3-(2-Amino-3-methyl-butyrylamino)-5-methyl-octanoic acid;

3-(2-Amino-3-methyl-butyrylamino)-5-methyl-nonanoic acid;
3-(2-Amino-3-methyl-butyrylamino)-4,5-dimethyl-heptanoic acid;
3-(2-Amino-3-methyl-butyrylamino)-4,5-dimethyl-octanoic acid;
3-(2-Amino-3-methyl-butyrylamino)-4,5-dimethyl-nonanoic acid;
3-(2-Amino-3-methyl-pentanoylamino)-5-methyl-heptanoic acid;
3-(2-Amino-3-methyl-pentanoylamino)-5-methyl-octanoic acid;
3-(2-Amino-3-methyl-pentanoylamino)-5-methyl-nonanoic acid;
3-(2-Amino-3-methyl-pentanoylamino)-4,5-dimethyl-heptanoic acid;
3-(2-Amino-3-methyl-pentanoylamino)-4,5-dimethyl-octanoic acid;
3-(2-Amino-3-methyl-pentanoylamino)-4,5-dimethyl-nonanoic acid;
3-(2-Amino-4-methyl-pentanoylamino)-5-methyl-heptanoic acid;
3-(2-Amino-4-methyl-pentanoylamino)-5-methyl-octanoic acid;
3-(2-Amino-4-methyl-pentanoylamino)-5-methyl-nonanoic acid;
3-(2-Amino-4-methyl-pentanoylamino)-4,5-dimethyl-heptanoic acid;
3-(2-Amino-4-methyl-pentanoylamino)-4,5-dimethyl-octanoic acid; and
3-(2-Amino-4-methyl-pentanoylamino)-4,5-dimethyl-nonanoic acid.

Even more preferred are compounds of formula V

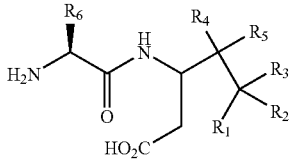

wherein, $R_1$, $R_2$, $R_3$, $R_4$, $R_5$, and $R_6$ are defined as above and wherein said compounds are selected from the following compounds and their pharmaceutically acceptable salts:
3-(2S-Amino-acetylamino)-5-methyl-heptanoic acid;
3-(2S-Amino-acetylamino)-5-methyl-octanoic acid;
3-(2S-Amino-acetylamino)-5-methyl-nonanoic acid;
3-(2S-Amino-acetylamino)-4,5-dimethyl-heptanoic acid;
3-(2S-Amino-acetylamino)-4,5-dimethyl-octanoic acid;
3-(2S-Amino-acetylamino)-4,5-dimethyl-nonanoic acid;
3-(2S-Amino-propionylamino)-5-methyl-heptanoic acid;
3-(2S-Amino-propionylamino)-5-methyl-octanoic acid;
3-(2S-Amino-propionylamino)-5-methyl-nonanoic acid;
3-(2S-Amino-propionylamino)-4,5-dimethyl-heptanoic acid;
3-(2S-Amino-propionylamino)-4,5-dimethyl-octanoic acid;
3-(2S-Amino-propionylamino)-4,5-dimethyl-nonanoic acid;
3-(2S-Amino-3-methyl-butyrylamino)-5-methyl-heptanoic acid;
3-(2S-Amino-3-methyl-butyrylamino)-5-methyl-octanoic acid;
3-(2S-Amino-3-methyl-butyrylamino)-5-methyl-nonanoic acid;
3-(2S-Amino-3-methyl-butyrylamino)-4,5-dimethyl-heptanoic acid;
3-(2S-Amino-3-methyl-butyrylamino)-4,5-dimethyl-octanoic acid;
3-(2S-Amino-3-methyl-butyrylamino)-4,5-dimethyl-nonanoic acid;
3-(2S-Amino-3-methyl-pentanoylamino)-5-methyl-heptanoic acid;
3-(2S-Amino-3-methyl-pentanoylamino)-5-methyl-octanoic acid;
3-(2S-Amino-3-methyl-pentanoylamino)-5-methyl-nonanoic acid;
3-(2S-Amino-3-methyl-pentanoylamino)-4,5-dimethyl-heptanoic acid;
3-(2S-Amino-3-methyl-pentanoylamino)-4,5-dimethyl-octanoic acid;
3-(2S-Amino-3-methyl-pentanoylamino)-4,5-dimethyl-nonanoic acid;
3-(2S-Amino-4-methyl-pentanoylamino)-5-methyl-heptanoic acid;
3-(2S-Amino-4-methyl-pentanoylamino)-5-methyl-octanoic acid;
3-(2S-Amino-4-methyl-pentanoylamino)-5-methyl-nonanoic acid;
3-(2S-Amino-4-methyl-pentanoylamino)-4,5-dimethyl-heptanoic acid;
3-(2S-Amino-4-methyl-pentanoylamino)-4,5-dimethyl-octanoic acid; and
3-(2S-Amino-4-methyl-pentanoylamino)-4,5-dimethyl-nonanoic acid.

Even more preferred are compounds of formula VI

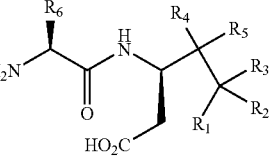

wherein, $R_1$, $R_2$, $R_3$, $R_4$, $R_5$, and $R_6$ are defined as above and wherein said compounds are selected from the following compounds and their pharmaceutically acceptable salts:
3-(2S-Amino-acetylamino)-5-methyl-heptanoic acid;
3S-(2S-Amino-acetylamino)-5-methyl-octanoic acid;
3S-(2S-Amino-acetylamino)-5-methyl-nonanoic acid;
3R-(2S-Amino-acetylamino)-4,5-dimethyl-heptanoic acid;
3R-(2S-Amino-acetylamino)-4,5-dimethyl-octanoic acid;
3R-(2S-Amino-acetylamino)-4,5-dimethyl-nonanoic acid;
3S-(2S-Amino-propionylamino)-5-methyl-heptanoic acid;
3S-(2S-Amino-propionylamino)-5-methyl-octanoic acid;
3S-(2S-Amino-propionylamino)-5-methyl-nonanoic acid;
3R-(2S-Amino-propionylamino)-4,5-dimethyl-heptanoic acid;
3R-(2S-Amino-propionylarnino)-4,5-dimethyl-octanoic acid;
3R-(2S-Amino-propionylamino)-4,5-dimethyl-nonanoic acid;
3S-(2S-Amino-3-methyl-butyrylamino)-5-methyl-heptanoic acid;
3S-(2S-Amino-3-methyl-butyrylamino)-5-methyl-octanoic acid;
3S-(2S-Amino-3-methyl-butyrylamino)-5-methyl-nonanoic acid;

3R-(2S-Amino-3-methyl-butyrylamino)-4,5-dimethyl-heptanoic acid;
3R-(2S-Amino-3-methyl-butyrylamino)-4,5-dimethyl-octanoic acid;
3R-(2S-Amino-3-methyl-butyrylamino)-4,5-dimethyl-nonanoic acid;
3S-(2S-Amino-3-methyl-pentanoylamino)-5-methyl-heptanoic acid;
3S-(2S-Amino-3-methyl-pentanoylamino)-5-methyl-octanoic acid;
3S-(2S-Amino-3-methyl-pentanoylamino)-5-methyl-nonanoic acid;
3R-(2S-Amino-3-methyl-pentanoylamino)-4,5-dimethyl-heptanoic acid;
3R-(2S-Amino-3-methyl-pentanoylamino)-4,5-dimethyl-octanoic acid;
3R-(2S-Amino-3-methyl-pentanoylamino)-4,5-dimethyl-nonanoic acid;
3S-(2S-Amino-4-methyl-pentanoylamino)-5-methyl-heptanoic acid;
3S-(2S-Amino-4-methyl-pentanoylamino)-5-methyl-octanoic acid;
3S-(2S-Amino-4-methyl-pentanoylamino)-5-methyl-nonanoic acid;
3R-(2S-Amino-4-methyl-pentanoylamino)-4,5-dimethyl-heptanoic acid;
3R-(2S-Amino4-methyl-pentanoylarnino)-4,5-dimethyl-octanoic acid;

and 3R-(2S-Amino4-methyl-pentanoylamino)-4,5-dimethyl-nonanoic acid.

This invention also relates to compounds of the formula VII and the pharmaceutically acceptable salts of such compounds.

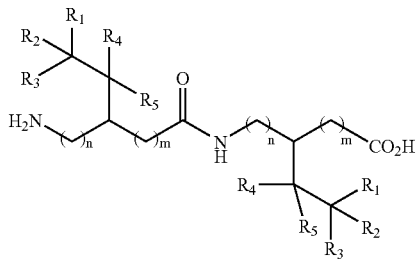

VII wherein, $R_1$, $R_2$, $R_3$, $R_4$, $R_5$, m and n are defined as above and $R_1$-$R_5$ and m and n can be the same or different at each occurrence and wherein said compounds are selected from the following compounds and their pharmaceutically acceptable salts:

3-(3-Amino-5-methyl-heptanoylamino)-5-methyl-heptanoic acid;
3-(3-Amino-5-methyl-octanoylamino)-5-methyl-octanoic acid; and
3-(3-Amino-5-methyl-nonanoylamino)-5-methyl-nonanoic acid.

This invention also relates to compounds of the formula VIII and the pharmaceutically acceptable salts of such compounds.

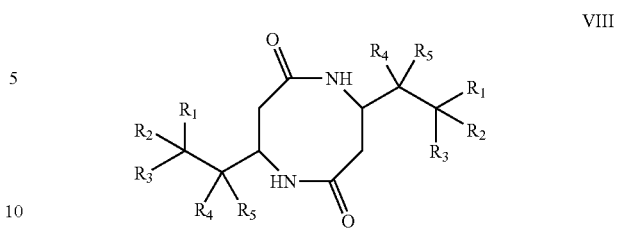

VIII wherein, $R_1$, $R_2$, $R_3$, $R_4$, and $R_5$ are defined as above and $R_1$-$R_5$ can be the same or different at each occurrence and wherein said compounds are selected from the following compounds and their pharmaceutically acceptable salts:

4,8-Bis-(2-methyl-butyl)-[1,5]-diazocane-2,6-dione;
4,8-Bis-(2-methyl-pentyl)-[1,5]-diazocane-2,6-dione; and
4,8-Bis-(2-methyl-hexyl)-[1,5]-diazocane-2,6-dione.

This invention also relates to a pharmaceutical composition comprising a therapeutically effective amount of a compound of the formula I, II, III, IV, V, VI, VII, or VIII, or a pharmaceutically acceptable salt thereof, and a pharmaceutically acceptable carrier.

This invention also relates to a method of treating a disorder or condition selected from epilepsy, faintness attacks, fibromyalgia, hypokinesia, cranial disorders, hot flashes, essential tremor, chemical dependencies and addictions, (e.g., dependencies on or addictions to alcohol, amphetamines (or amphetamine-like substances) caffeine, cannabis, cocaine, heroin, hallucinogens, tobacco, inhalants and aerosol propellants, nicotine, opioids, phenylglycidine derivatives, sedatives, hypnotics, benzodiazepines and other anxiolytics), and withdrawal symptoms associated with such dependencies or addictions, addictive behaviors such as gambling; migraine, spasticity, arthritis, irritable bowel syndrome (IBS), chronic pain, acute pain, neuropathic pain, vascular headache, sinus headache, inflammatory disorders (e.g., rheumatoid arthritis, osteoarthritis, psoriasis) diuresis, premenstrual syndrome, premenstrual dysphoric disorder, tinnitus, and gastric damage in a mammal, including a human, comprising administering to a mammal in need of such treatment a therapeutically effective amount of a compound of the formula I, II, II, IV, V, VI, VII, or VIII, or a pharmaceutically acceptable salt thereof.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia, such as those that occur in patients undergoing carotid endarterectomy or other cerebrovascular or vascular surgical procedures, or diagnostic vascular procedures including cerebral angiography and the like.

Compounds of the formula I, II, III, IV, V, VI, VII, or VIII are also useful in the treatment of head trauma, spinal cord trauma, or injury from general anoxia, hypoxia, hypoglycemia, hypotension as well as similar injuries seen during procedures from embole, hyperfusion, and hypoxia. They are also useful in preventing neuronal damage that occurs during cardiac bypass surgery, in incidents of intracranial hemorrhage, in perinatal asphyxia, in cardiac arrest, and status epilepticus.

This invention also relates to a method of treating a disorder or condition selected from the group consisting of delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies; movement disorders such as akinesias, dyskinesias, including familial paroxysmal dyskinesias, spasticities, Tourette's syndrome, Scott syndrome, PAL-SYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; Down's syndrome; demyelinating diseases such as multiple sclerosis (MS) and amylolateral sclerosis (ALS), peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema in a mammal, including a human, comprising administering to said mammal an amount of a compound of the formula I, II, III, IV, V, VI, VII, or VIII, or a pharmaceutically acceptable salt thereof, that is effective in treating such disorder or condition.

Pain refers to acute as well as chronic pain. Acute pain is usually short-lived and is associated with hyperactivity of the sympathetic nervous system. Examples are postoperative pain and allodynia. Chronic pain is usually defined as pain persisting from 3 to 6 months and includes somatogenic pain and psychogenic pain. Other pain is nociceptive.

Examples of the types of pain that can be treated with the compounds of formulas I, II, III, IV, V, VI, VII, or VIII, of the present invention and their pharmaceutically acceptable salts include pain resulting from soft tissue and peripheral damage, such as acute trauma, pain associated with osteoarthritis and rheumatoid arthritis, musculo-skeletal pain, such as pain experienced after trauma; spinal pain, dental pain, myofascial pain syndromes, episiotomy pain, and pain resulting from burns; deep and visceral pain, such as heart pain, muscle pain, eye pain, orofacial pain, for example, odontalgia, abdominal pain, gynaecological pain, for example, dysmenorrhoea, labour pain and pain associated with endometriosis; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, trigeminal neuralgia, neuropathic lower back pain, HIV related neuropathic pain, cancer related neuropathic pain, diabetic neuropathic pain, and arachnoiditis; neuropathic and non-neuropathic pain associated with carcinoma, often referred to as cancer pain; central nervous system pain, such as pain due to spinal cord or brain stem damage; lower back pain; sciatica; phantom limb pain, headache, including migraine and other vascular headaches, acute or chronic tension headache, cluster headache, temperomandibular pain and maxillary sinus pain; pain resulting from ankylosing spondylitis and gout; pain caused by increased bladder contractions; post operative pain; scar pain; and chronic non-neuropathic pain such as pain associated with fibromyalgia, HIV, rheumatoid and osteoarthritis, anthralgia and myalgia, sprains, strains and trauma such as broken bones; and post surgical pain.

Still other pain is caused by injury or infection of peripheral sensory nerves. It includes, but is not limited to pain from peripheral nerve trauma, herpes virus infection, diabetes mellitus, fibromyalgia, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain syndrome.

The compounds of the invention are also useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

This invention also relates to a method of treating a disorder or condition selected from the group consisting of mood disorders, such as depression, or more particularly, depressive disorders, for example, single episodic or recurrent major depressive disorders, dysthymic disorders, depressive neurosis and neurotic depression, melancholic depression, including anorexia, weight loss, insomnia, early morning waking and psychomotor retardation, atypical depression (or reactive depression), including increased appetite, hypersomnia, psychomotor agitation or irritability, seasonal affective disorder and pediatric depression; or bipolar disorders or manic depression, for example, bipolar I disorder, bipolar II disorder and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety disorder, social phobia, obsessive-compulsive disorder, stress disorders, including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder, mood disorders associated with schizophrenia; behavioral disturbances associated with mental retardation, autistic disorder, and conduct disorder in a mammal, including a human, comprising administering to said mammal an amount of a compound of the formula I, II, III, IV, V, VI, VII, or VIII, or a pharmaceutically acceptable salt thereof, that is effective in treating such disorder or condition.

The compounds of the invention are also useful in the treatment of sleep disorders. Sleep disorders are disturbances that affect the ability to fall and/or stay asleep, that involves sleeping too much, or that result in abnormal behavior associated with sleep. The disorders include, for example, insomnia, drug-associated sleeplessness, hypersomnia, narcolepsy, sleep apnea syndromes, and parasomnias.

This invention also relates to a method of treating a disorder or condition selected from the group consisting of sleep disorders (e.g., insomnia, drug-associated sleeplessness, REM sleep disorders, hypersomnia, narcolepsy, sleep-wake cycle disorders, sleep apnea syndromes, parasomnias, and sleep disorders associated with shift work and irregular work hours) a mammal, including a human, comprising administering to said mammal an amount of a compound of the formula I, II, III, IV, V, VI, VII, or VIII, or a pharmaceutically acceptable salt thereof, that is effective in treating such disorder or condition.

Compounds of formulas I, II, I, IV, V, VI, VII, or VIII contain at least one chiral center and therefore may exist in different enantiomeric and diastereomeric forms. This invention relates to all optical isomers and all stereoisomers of compounds of the formulas I, II, III, IV, V, VI, VII, or VIII both as racemic mixtures and as individual enantiomers and diastereoisomers of such compounds, and mixtures thereof, and to all pharmaceutical compositions and methods of treatment defined above that contain or employ them, respectively. Compounds with one stereocenters can exist in either racemic form, as a mixture of isomers, or as S or R stereochemistry. Compounds with two stereocenters can exist in either racemic form, as a mixture of isomers, or as SR, SS, RS, or RR stereochemistry. Compounds with three stereocenters can exist in either racemic form, as a mixture of isomers, or as RRR, SRR, RSR, RRS, SSS, RSS, SRS, or SSR stereochemistry. Individual isomers can be obtained by known methods, such as optical resolution, optically selective reaction, or chromatographic separation in the preparation of the final product or its intermediate. Individual enantiomers of the compounds of this invention may have advantages, as compared with the racemic mixtures of these compounds, in the treatment of various disorders or conditions.

The present invention also includes isotopically labelled compounds, which are identical to those recited in formulas I, II, III, IV, V, VI, VII, or VIII but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbomyl, and the like.

The term "alkoxy", as used herein, unless otherwise indicated, means "alkyl-O—", wherein "alkyl" is as defined above. Examples of "alkoxy" groups include, but are not limited to, methoxy, ethoxy, propoxy, butoxy and pentoxy.

The term "treating", as used herein, refers to reversing, alleviating, inhibiting the progress of, or preventing the disorder or condition to which such term applies, or preventing one or more symptoms of such condition or disorder. The term "treatment", as used herein, refers to the act of treating, as "treating" is defined immediately above.

The term "natural α-amino acid", as used herein, refers to one of the twenty naturally occurring or endogenous amino acids. Examples of "naturally occurring α-amino acids" include, but are not limited to, glycine, alanine, valine, leucine, isoleucine, proline, serine, threonine, lysine, phenylalanine, and the like.

The terms "$R_1$-$R_5$ and m and n can be the same or different at each occurrence" and "$R_1$-$R_5$ can be the same or different at each occurrence", as used herein, mean that for those compounds of formulae VII and VIII, respectively, where $R_1$-$R_5$ occur twice in the structure, that each $R_1$-$R_5$ can be selected independently of the other and the same for m and n. For example, $R_1$ can be a methyl group on one side of the molecule and can be an ethyl group on the other side of the same molecule.

Because amino acids are amphoteric, pharmacologically compatible salts can be salts of appropriate inorganic or organic acids, for example, hydrochloric, sulphuric, phosphoric, acetic, oxalic, lactic, citric, malic, salicylic, malonic, maleic, succinic, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

DETAILED DESCRIPTION OF THE INVENTION

The preparation of compounds of this invention that are not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i e., about 1 atmosphere, is preferred as a matter of convenience.

The compounds of the formula 1 and the Group A compounds, and the intermediates shown in the above reaction schemes can be isolated and purified by conventional procedures, such as recrystallization or chromatographic separation.

The radioligand binding assay using [$^3$H]-gabapentin and the $\alpha 2\delta$-subunit derived from porcine brain tissue was used (See, Gee, Nicolas S et al. "*The novel anticonvulsant drug, gabapentin (Neurontin), binds to the $\alpha 2\delta$ subunit of a calcium channel*". *J. Biol. Chem.* (1996), 271(10), 5768-76).

The In vivo activity of compounds of this invention can be determined in animal models of hyperalgesia (See Sluka, K., et al. 2001, "Unilateral Intramuscular Injections Of Acidic Saline Produce A Bilateral, Long-Lasting Hyperalgesia", *Muscle Nerve* 24: 37-46; Dixon, W., 1980, "Efficient analysis of experimental observations". *Ann Rev Pharmacol Toxicol* 20:441-462; Randall L. O. and Selitto J. J., "A Method For Measurement Of Analgesic Activity On Inflamed Tissue," *Arch. Int. Pharmacodyn,* 1957;4:409-419; Hargreaves K., Dubner R., Brown F., Flores C., and Joris J. "A New And Sensitive Method For Measuring Thermal Nociception In Cutaneous Hyperalgesia". *Pain.* 32:77-88, 1988.), anxiety (Vogel J. R., Beer B., and Clody D. E., "A Simple And Reliable Conflict Procedure For Testing Anti-Anxiety Agents", *Psychopharmacologia* 21:1-7, 1971), The compounds of the present invention, and their pharmaceutically acceptable salts, can be administered to mammals via either the oral, parenteral (such as subcutaneous, intravenous, intramuscular, intrasternal and infusion techniques), rectal, buccal or intranasal routes.

The novel compounds of the present invention may be administered alone or in combination with pharmaceutically acceptable carriers or diluents by any of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, suppositories, jellies, gels, pastes, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the weight ratio of the novel compounds of this invention to the pharmaceutically acceptable carrier will be in the range from about 1:6 to about 2:1, and preferably from about 1:4 to about 1:1.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intra-muscular and subcutaneous injection purposes. The preparation of all these solutions under sterile conditions is readily accomplished by standard pharmaceutical techniques well known to those skilled in the art.

For intranasal administration or administration by inhalation, the novel compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch. Formulations of the active compounds of this invention for treatment of the conditions referred to above in the average adult human are preferably arranged so that each metered dose or "puff" of aerosol contains 20 µg to 1000 µg of active compound. The overall daily dose with an aerosol will be within the range 100 µg to 10 mg. Administration may be several times daily, for example 2, 3, 4 or 8 times, giving for example, 1, 2 or 3 doses each time.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of formula I, II, III, or IV or a corresponding pharmaceutically acceptable salt of such compound.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material. In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.01 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.1 mg to about 1 g daily. The dosages, however, may be varied depending upon the requirements of the patient, the severity of the condition being treated, and the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

The permeability of compounds of the invention from apical (A) to basal (B) (lumenal to blood side) and from basal (B) to apical side (A) are shown in the table below. Metoprolol was used as a positive marker. Mannitol was used as a negative marker since it appears to be absorbed through the paracellular rather than the transcellular pathway. Cell transport, and efflux studies were conducted with Caco-2 cells grown on Snapwells between 22 to 28 days postseeding. Typically, 10 mM MES buffer (pH 6.5) with 5 mM KCl, 135 mM NaCl, 1.8 mM CaCl$_2$, and 5 mM D-glucose was used for the AP side and 10 mM MOPS (pH 7.4) with 5 mM KCl, 132.5 mM NaCl, 1.8 mM CaCl$_2$, and 5 mM D-glucose was used for the BL side. After washing the monolayers, drug-free media at the appropriate pH (pH 7.4 or 6.5) were first added to both compartments to allow the cells to equilibrate for approximately 15 min at 37° C. Transport studies were then conducted using 1.5 mL of transport media in the apical side and 2.5 mL in the basolateral side. The donor solution containing the probe compound was added to either the apical or basolateral compartment. Plates were placed in a shaking incubator (Boekel Scientific, Feasterville, Pa.) at 37° C. during the experiments. Transport in both apical-to-basolateral (A-to-B) and basolateral-to-apical (B-to-A) directions was measured for each drug. Aliquots were removed from the nondosing compartment at predetermined time points and replaced with fresh medium to maintain a constant volume. During studies with radiolabeled compounds, 100 uL samples were taken at each time point. The apparent permeability coefficients ($P_{app}$) were calculated using the following equation: Papp=dQ/dtX1/CoX1/A, where dQ/dt is the permeability rate, $C_o$ is the initial concentration in the donor compartment, and A is the surface area of the membrane. Flux rates (dQ/dt×1/A) were calculated by plotting the amount transported per unit area as a function of time and determining the slope of the line using linear regression. The permeability of 3S-[(2S-Amino4-methyl-pentanoylamino)-methyl]-5R-methyl-nonanoic acid was evaluated in Caco-2 at a concentration of 10 uM. The Caco-2 permeabilities of 3S-[(2S-Amino-4-methyl-pentanoylamino)-methyl]-5R-methyl-nonanoic acid was 0.74× 10-6 cm/s in the apical to basolateral (A®B) direction and are lower than that of metoprolol (which is >90% absorbed in humans). Furthermore, the ratio of B to A/A to B in Caco-2 permeability is less than 1 over the concentration of 10 uM, indicating that 3S-[(2S-Amino-4-methyl-pentanoylamino)-methyl]-5R-methyl-nonanoic acid is unlikely to be a substrate for efflux.

| Compound | A to B | | B to A | | |
|---|---|---|---|---|---|
| | Peff * 10$^{-6}$ | Stdev * 10$^{-6}$ | Peff * 10 | Stdev * 10$^{-6}$ | Ratio |
| 3S-[(2S-Amino-4-methyl-pentanoylamino)-methyl]-5R-methyl-nonanoic acid | 0.74 | 1.28 | 0.05 | 0.06 | 0.07 |
| Metoprolol | 8.74 | 1.10 | 20.26 | 3.38 | 2.32 |
| Mannitol | 1.81 | 0.68 | 1.41 | 0.35 | 0.78 |

The following Examples illustrate the preparation of the compounds of the present invention. They are not meant to be limiting in scope. Melting points are uncorrected. NMR data are reported in parts per million and are referenced to the deuterium lock signal from the sample solvent.

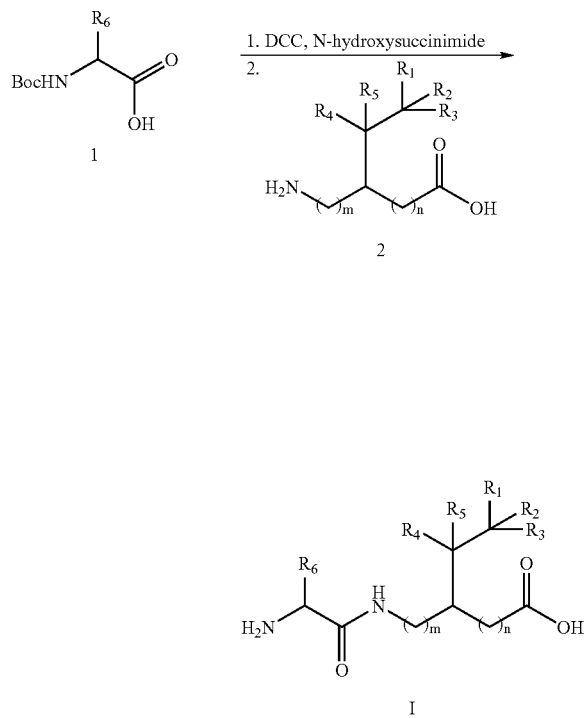

Compounds of the invention can be prepared by methods generally known in the art (see *J. Am. Chem. Soc.*, 89, 7151, 1967). A compound of formula I can be prepared from a compound of formula 1 through treatment of a compound of formula 1 with N,N'-dicyclohexylcarbodiimide (DCC) and N-hydroxysuccinimide in a solvent such as water, tetrahydrofuran, acetonitrile or water/acetonitrile in the presence of a suitable base such as sodium hydroxide or alike followed by treatment with a compound of formula 2.

EXAMPLE 1

3-[(2-tert-Butoxycarbonylamino-4-methyl-pentanoylamino)-methyl]-5-methyl-octanoic acid 2-tert-Butoxycarbonylamino-4-methyl-pentanoic acid 2,5-dioxo-cyclopentyl ester (2)

To the mixture of N-(tert-Butoxycarbonyl)-L-leucine (1.03 g, 4.46 mmol) and N-Hydroxysuccinimide (0.74 g, 6.43 mmol) in acetonitrile (30 ml) was added 1,3-Dicyclohexylcarbodiimide (1.24 g, 6.01 mmol) and stirred for 4 hr, at room temperature. The resulting precipitate was filtered off and the acetonitrile filtrate containing 2 was carried on to the next step. MS, m/z (relative intensity): 327 [M+1H, 100%], 327 [M+1H —C(CH$_3$)$_3$, 100%].

3-[(2-tert-Butoxycarbonylamino-4-methyl-pentanoylamino)-methyl]-5-methyl-octanoic acid (Example 1)

To a solution of (3S,5R)-3-Aminomethyl-5-methyl-octanoic acid (1.0 g, 5.34 mmol) in sodium hydroxide (0.45 g, 11.3 mmol) and water (30 ml) was added a solution of 2 (1.50, 4.46 mmol) in acetonitrile, and the mixture was stirred at room temperature for 24 hr. The solution was concentrated to dryness and the resulting residue was chromatographed with 5% methanol in dichloromethane. The resulting residue was dissolved in a mixture trifluoroacetic acid (25 ml) and dichloromethane (25 ml) and stir at room temperature for 1 hr. The solution was evaporated to dryness and the resulting residue was applied to BondElute SCX ion exchange resin. The resin was eluted with water until the eluent was at constant $_p$H of 6.5 and it was then eluted with a 1:1 solution of methanol and 10% ammonium hydroxide solution. The ammonium hydroxide solution was evaporated and the residue was recrystalized from methanol-acetonitrile mixture to afford example 1 (0.70 g, 52.3%) as a white solid. 1H NMR (400 MHz, METHANOL-D4) δ ppm 0.9 (m, 6H) 1.0 (t, J=7.1 6H) 1.1 (m, 2H) 1.3 (m, 4H) 1.6 (m, 2H) 1.7 (m, 2H) 2.1 (s, 3H) 3.1 (dd, J=13.4, 7.6 Hz, 1H) 3.2 (dd, J=13.2, 3.9 Hz, 1H) 3.7 (m, 1H). MS, m/z (relative intensity): 301[M+1H, 100%], 299 [M−1H, 100%].

| Compound Name | Mass Spec | 1H NMR (400 MHz, METHANOL-D4) δ ppm |
|---|---|---|
| 3S[(2Stert-Butoxycarbonylamino-4-methyl-pentanoylamino)-methyl]-5Rmethyl-octanoic acid | MS, m/z(relative intensity): 301[M+1H, 100%], 299[M−1H, 100%]. | 0.9(m, 6H) 1.0(t, J=7.1 6H) 1.1(m, 2H) 1.3(m, 4H) 1.6(m, 2H) 1.7(m, 2H) 2.1(s, 3H) 3.1(dd, J=13.4, 7.6Hz, 1H) 3.2(dd, J=13.2, 3.9Hz, 1H) 3.7(m, 1H) |
| 3S[(2RAmino-3-methyl-butyrylamino)-methyl]-5Rmethyl-octanoic acid | MS, m/z(relative intensity): 287[M+1H, 100%], 285[M−1H, 100%]. | 0.8(dd, J=8.7, 7.0Hz, 6H) 0.9(d, 6H) 1.0(m, 3H) 1.2(m, 4H) 1.4(m, 1H) 2.0(m, 3H) 2.9(m, 1H) 3.2(dd, J=13.2, 3.2Hz, 1H) 3.3(d, J=6.3Hz, 1H) |
| 3S[(2-Amino-3-methyl-butyrylamino)-methyl]-5Rmethyl-octanoic acid | MS, m/z(relative intensity): 287[M+1H, 100%], 285[M−1H, 100%]. | 0.8(m, 7H) 1.0(m, 6H) 1.2(m, 4H) 1.5(m, 2H), 2.2(m, 3H) 3.1(m, 2H) 3.3(m, 1H) |
| 3S[(2SAmino-3-methyl-pentanoylamino)-methyl]-5Rmethyl-octanoic acid | MS, m/z(relative intensity): 301[M+1H, 100%], 299[M−1H, 100%]. | 0.8(dd, J=6.7, 4.3Hz, 6H) 0.9(m, 6H) 1.0(m, 2H) 1.2(m, 5H) 1.5(m, 2H) 1.8(br, 1H) 2.1(m, 4H) 3.0(br, 1H) 3.2(d, J=11.7Hz, 1H) |
| 3S[(2SAmino-4-methyl-pentanoylamino)-methyl]-5Rmethyl-nonanoic acid | MS, m/z(relative intensity): 315[M+1H, 100%], 313[M−1H, 100%]. | 0.8(m, 6H) 0.9(dd, J=9.6, 4.8Hz, 6H) 1.0(m, 2H) 1.2(m, 7H) 1.5(br, 4H) 2.1(br, 3H) 3.0(m, 1H) 3.2(m, 1H) |
| 3R[(2Smino-4-methyl-pentanoylamino)-methyl]- | MS, m/z(relative intensity): 287[M+1H, | 0.8(dd, J=15.7, 6.7Hz, 6H) 0.9(d, J=6.3Hz, 6H) 0.9(m, 3H) 1.2(m, 3H) 1.5(m, 4H) 2.2(m, |

-continued

| Compound Name | Mass Spec | 1H NMR (400 MHz, METHANOL-D4) δ ppm |
|---|---|---|
| 4Rimethyl-hexanoic acid | 100%], 285[M−1H, 100%]. | 2H) 3.1(m, 2H) |
| 3R[(2SAmino-3-methyl-butyrylamino)-methyl]-4R5-dimethyl-hexanoic acid | MS, m/z(relative intensity): 273[M+1H, 100%], 271[M−1H, 100%]. | 0.8(dd, J=15.7, 6.5Hz, 6H) 0.9(d, J=6.6Hz, 6H) 1.0(s, 4H) 1.2(m, 1H) 1.5(m, 1H) 2.2(br, 4H) 3.1(s, 2H) |

The In vivo activity of a compound of this invention was determined in an animal model of anxiety as set forth in Vogel J R, Beer B., and Clody D E, "A Simple And Reliable Conflict Procedure For Testing Anti-Anxiety Agents", *Psychopharmacologia* 21:1-7, 1971).

Compound

3S-[(2S-Amino-4-methyl-pentanoylamino)-methyl]-5R-methyl-octanoic acid

Anxiolytic Activity (Vogel conflict model, 30 mg/kg, PO, percent reference activity compared to pregabalin) was found to be 138.10.

What is claimed is:

1. A compound selected from the group consisting of the following compounds and their pharmaceutically acceptable salts:
    3-[(2-Amino-4-methyl-pentanoylamino)-methyl]-5-methyl-octanoic acid;
    3-[(2-Amino-4-methyl-pentanoylamino)-methyl]-5-methyl-heptanoic acid;
    3-[(2-Amino-4-methyl-pentanoylamino)-methyl]-5-methyl-nonanoic acid;
    3-[(2-Amino-4-methyl-pentanoylamino)-methyl]-4,5-dimethyl-heptanoic acid;
    3-[(2-Amino-4-methyl-pentanoylamino)-methyl]-4,5-dimethyl-octanoic acid;
    3-[(2-Amino-4-methyl-pentanoylamino)-methyl]-4,5-dimethyl-nonanoic acid;
    3-[(2-Amino-4-methyl-pentanoylamino)-methyl]-5-methyl-hexanoic acid;
    3-[(2-Amino-4-methyl-pentanoylamino)-methyl]-4,5-dimethyl-hexanoic acid;
    3-[(2-Amino-3-methyl-pentanoylamino)-methyl]-5-methyl-heptanoic acid;
    3-[(2-Amino-3-methyl-pentanoylamino)-methyl]-5-methyl-octanoic acid;
    3-[(2-Amino-3-methyl-pentanoylamino)-methyl]-5-methyl-nonanoic acid;
    3-[(2-Amino-3-methyl-pentanoylamino)-methyl]-4,5-dimethyl-heptanoic acid;
    3-[(2-Amino-3-methyl-pentanoylamino)-methyl]-4,5-dimethyl-octanoic acid;
    3-[(2-Amino-3-methyl-pentanoylamino)-methyl]-4,5-dimethyl-nonanoic acid;
    3-[(2-Amino-3-methyl-pentanoylamino)-methyl]-5-methyl-hexanoic acid;
    3-[(2-Amino-3-methyl-pentanoylamino)-methyl]-4,5-dimethyl-hexanoic acid;
    3-[(2-Amino-3-methyl-butyrylamino)-methyl]-5-methyl-heptanoic acid;
    3-[(2-Amino-3-methyl-butyrylamino)-methyl]-5-methyl-octanoic acid;
    3-[(2-Amino-3-methyl-butyrylamino)-methyl]-5-methyl-nonanoic acid;
    3-[(2-Amino-3-methyl-butyrylamino)-methyl]-4,5-dimethyl-heptanoic acid;
    3-[(2-Amino-3-methyl-butyrylamino)-methyl]-4,5-dimethyl-octanoic acid;
    3-[(2-Amino-3-methyl-butyrylamino)-methyl]-4,5-dimethyl-nonanoic acid;
    3-[(2-Amino-3-methyl-butyrylamino)-methyl]-5-methyl-hexanoic acid;
    3-[(2-Amino-3-methyl-butyrylamino)-methyl]-4,5-dimethyl-hexanoic acid;
    3-[(2-Amino-propionylamino)-methyl]-5-methyl-heptanoic acid;
    3-[(2-Amino-propionylamino)-methyl]-5-methyl-octanoic acid;
    3-[(2-Amino-propionylamino)-methyl]-5-methyl-nonanoic acid;
    3-[(2-Amino-propionylamino)-methyl]-4,5-dimethyl-heptanoic acid;
    3-[(2-Amino-propionylamino)-methyl]-4,5-dimethyl-octanoic acid;
    3-[(2-Amino-propionylamino)-methyl]-4,5-dimethyl-nonanoic acid;
    3-[(2-Amino-propionylamino)-methyl]-5-methyl-hexanoic acid;
    3-[(2-Amino-propionylamino)-methyl]-4,5-dimethyl-hexanoic acid;
    3-[(2-Amino-acetylamino)-methyl]-5-methyl-heptanoic acid;
    3-[(2-Amino-acetylamino)-methyl]-5-methyl-octanoic acid;
    3-[(2-Amino-acetylamino)-methyl]-5-methyl-heptanoic acid;
    3-[(2-Amino-acetylamino)-methyl]-4,5-dimethyl-heptanoic acid;
    3-[(2-Amino-acetylamino)-methyl]-4,5-dimethyl-octanoic acid;
    3-[(2-Amino-acetylamino)-methyl]-4,5-dimethyl-nonanoic acid;
    3-[(2-Amino-acetylamino)-methyl]-5-methyl-hexanoic acid;
    3-[(2-Amino-acetylamino)-methyl]-4,5-dimethyl-hexanoic acid;
    3-(2-Amino-acetylamino)-5-methyl-heptanoic acid;
    3-(2-Amino-acetylamino)-5-methyl-octanoic acid;
    3-(2-Amino-acetylamino)-5-methyl-nonanoic acid;
    3-(2-Amino-acetylamino)-4,5-dimethyl-heptanoic acid;
    3-(2-Amino-acetylamino)-4,5-dimethyl-octanoic acid;
    3-(2-Amino-acetylamino)-4,5-dimethyl-nonanoic acid;
    3-(2-Amino-propionylamino)-5-methyl-heptanoic acid;
    3-(2-Amino-propionylamino)-5-methyl-octanoic acid;
    3-(2-Amino-propionylamino)-5-methyl-nonanoic acid;
    3-(2-Amino-propionylamino)-4,5-dimethyl-heptanoic acid;

3-(2-Amino-propionylamino)-4,5-dimethyl-octanoic acid;
3-(2-Amino-propionylamino)-4,5-dimethyl-nonanoic acid;
3-(2-Amino-3-methyl-butyrylamino)-5-methyl-heptanoic acid;
3-(2-Amino-3-methyl-butyrylamino)-5-methyl-octanoic acid;
3-(2-Amino-3-methyl-butyrylamino)-5-methyl-nonanoic acid;
3-(2-Amino-3-methyl-butyrylamino)-4,5-dimethyl-heptanoic acid;
3-(2-Amino-3-methyl-butyrylamino)-4,5-dimethyl-octanoic acid;
3-(2-Amino-3-methyl-butyrylamino)-4,5-dimethyl-nonanoic acid;
3-(2-Amino-3-methyl-pentanoylamino)-5-methyl-heptanoic acid;
3-(2-Amino-3-methyl-pentanoylamino)-5-methyl-octanoic acid;
3-(2-Amino-3-methyl-pentanoylamino)-5-methyl-nonanoic acid;
3-(2-Amino-3-methyl-pentanoylamino)-4,5-dimethyl-heptanoic acid;
3-(2-Amino-3-methyl-pentanoylamino)-4,5-dimethyl-octanoic acid;
3-(2-Amino-3-methyl-pentanoylamino)-4,5-dimethyl-nonanoic acid;
3-(2-Amino-4-methyl-pentanoylamino)-5-methyl-heptanoic acid;
3-(2-Amino-4-methyl-pentanoylamino)-5-methyl-octanoic acid;
3-(2-Amino4-methyl-pentanoylamino)-5-methyl-nonanoic acid;
3-(2-Amino4-methyl-pentanoylamino)-4,5-dimethyl-heptanoic acid;
3-(2-Amino4-methyl-pentanoylamino)-4,5-dimethyl-octanoic acid; and
3-(2-Amino4-methyl-pentanoylamino)-4,5-dimethyl-nonanoic acid.

2. A compound selected from the group consisting of the following compounds and their pharmaceutically acceptable salts:

3-[(2S-Amino-4-methyl-pentanoylamino)-methyl]-5-methyl-octanoic acid;
3-[(2S-Amino-4-methyl-pentanoylamino)-methyl]-5-methyl-heptanoic acid;
3-[(2S-Amino-4-methyl-pentanoylamino)-methyl]-5-methyl-nonanoic acid;
3-[(2S-Amino-4-methyl-pentanoylamino)-methyl]-4,5-dimethyl-heptanoic acid;
3-[(2S-Amino-4-methyl-pentanoylamino)-methyl]-4,5-dimethyl-octanoic acid;
3-[(2S-Amino-4-methyl-pentanoylamino)-methyl]-4,5-dimethyl-nonanoic acid;
3-[(2S-Amino-4-methyl-pentanoylamino)-methyl]-5-methyl-hexanoic acid;
3-[(2S-Amino-4-methyl-pentanoylamino)-methyl]-4,5-dimethyl-hexanoic acid;
3-[(2S-Amino-3-methyl-pentanoylamino)-methyl]-5-methyl-heptanoic acid;
3-[(2S-Amino-3-methyl-pentanoylamino)-methyl]-5-methyl-octanoic acid;
3-[(2S-Amino-3-methyl-pentanoylamino)-methyl]-5-methyl-nonanoic acid;
3-[(2S-Amino-3-methyl-pentanoylamino)-methyl]-4,5-dimethyl-heptanoic acid;
3-[(2S-Amino-3-methyl-pentanoylamino)-methyl]-4,5-dimethyl-octanoic acid;
3-[(2S-Amino-3-methyl-pentanoylamino)-methyl]-4,5-dimethyl-nonanoic acid;
3-[(2S-Amino-3-methyl-pentanoylamino)-methyl]-5-methyl-hexanoic acid;
3-[(2S-Amino-3-methyl-pentanoylamino)-methyl]-4,5-dimethyl-hexanoic acid;
3-[(2S-Amino-3-methyl-butyrylamino)-methyl]-5-methyl-heptanoic acid;
3-[(2S-Amino-3-methyl-butyrylamino)-methyl]-5-methyl-octanoic acid;
3-[(2S-Amino-3-methyl-butyrylamino)-methyl]-5-methyl-nonanoic acid;
3-[(2S-Amino-3-methyl-butyrylamino)-methyl]-4,5-dimethyl-heptanoic acid;
3-[(2S-Amino-3-methyl-butyrylamino)-methyl]-4,5-dimethyl-octanoic acid;
3-[(2S-Amino-3-methyl-butyrylamino)-methyl]-4,5-dimethyl-nonanoic acid;
3-[(2S-Amino-3-methyl-butyrylamino)-methyl]-5-methyl-hexanoic acid;
3-[(2S-Amino-3-methyl-butyrylamino)-methyl]-4,5-dimethyl-hexanoic acid;
3-[(2S-Amino-propionylamino)-methyl]-5-methyl-heptanoic acid;
3-[(2S-Amino-propionylamino)-methyl]-5-methyl-octanoic acid;
3-[(2S-Amino-propionylamino)-methyl]-5-methyl-nonanoic acid;
3-[(2S-Amino-propionylamino)-methyl]-4,5-dimethyl-heptanoic acid;
3-[(2S-Amino-propionylamino)-methyl]-4,5-dimethyl-octanoic acid;
3-[(2S-Amino-propionylamino)-methyl]-4,5-dimethyl-nonanoic acid;
3-[(2S-Amino-propionylamino)-methyl]-5-methyl-hexanoic acid;
3-[(2S-Amino-propionylamino)-methyl]-4,5-dimethyl-hexanoic acid;
3-[(2S-Amino-acetylamino)-methyl]-5-methyl-heptanoic acid;
3-[(2S-Amino-acetylamino)-methyl]-5-methyl-octanoic acid;
3-[(2S-Amino-acetylamino)-methyl]-5-methyl-heptanoic acid;
3-[(2S-Amino-acetylamino)-methyl]-4,5-dimethyl-heptanoic acid;
3-[(2S-Amino-acetylamino)-methyl]-4,5-dimethyl-octanoic acid;
3-[(2S-Amino-acetylamino)-methyl]-4,5-dimethyl-nonanoic acid;
3-[(2S-Amino-acetylamino)-methyl]-5-methyl-hexanoic acid;
3-[(2S-Amino-acetylamino)-methyl]-4,5-dimethyl-hexanoic acid;
3-(2S-Amino-acetylamino)-5-methyl-heptanoic acid;
3-(2S-Amino-acetylamino)-5-methyl-octanoic acid;
3-(2S-Amino-acetylamino)-5-methyl-nonanoic acid;
3-(2S-Amino-acetylamino)-4,5-dimethyl-heptanoic acid;
3-(2S-Amino-acetylamino)-4,5-dimethyl-octanoic acid;
3-(2S-Amino-acetylamino)-4,5-dimethyl-nonanoic acid;
3-(2S-Amino-propionylamino)-5-methyl-heptanoic acid;
3-(2S-Amino-propionylamino)-5-methyl-octanoic acid;
3-(2S-Amino-propionylamino)-5-methyl-nonanoic acid;
3-(2S-Amino-propionylamino)-4,5-dimethyl-heptanoic acid;

3-(2S-Amino-propionylamino)-4,5-dimethyl-octanoic acid;
3-(2S-Amino-propionylamino)-4,5-dimethyl-nonanoic acid;
3-(2S-Amino-3-methyl-butyrylamino)-5-methyl-heptanoic acid;
3-(2S-Amino-3-methyl-butyrylamino)-5-methyl-octanoic acid;
3-(2S-Amino-3-methyl-butyrylamino)-5-methyl-nonanoic acid;
3-(2S-Amino-3-methyl-butyrylamino)-4,5-dimethyl-heptanoic acid;
3-(2S-Amino-3-methyl-butyrylamino)-4,5-dimethyl-octanoic acid;
3-(2S-Amino-3-methyl-butyrylamino)-4,5-dimethyl-nonanoic acid;
3-(2S-Amino-3-methyl-pentanoylamino)-5-methyl-heptanoic acid;
3-(2S-Amino-3-methyl-pentanoylamino)-5-methyl-octanoic acid;
3-(2S-Amino-3-methyl-pentanoylamino)-5-methyl-nonanoic acid;
3-(2S-Amino-3-methyl-pentanoylamino)-4,5-dimethyl-heptanoic acid;
3-(2S-Amino-3-methyl-pentanoylamino)-4,5-dimethyl-octanoic acid;
3-(2S-Amino-3-methyl-pentanoylamino)-4,5-dimethyl-nonanoic acid;
3-(2S-Amino-4-methyl-pentanoylamino)-5-methyl-heptanoic acid;
3-(2S-Amino-4-methyl-pentanoylamino)-5-methyl-octanoic acid;
3-(2S-Amino-4-methyl-pentanoylamino)-5-methyl-nonanoic acid;
3-(2S-Amino-4-methyl-pentanoylamino)-4,5-dimethyl-heptanoic acid;
3-(2S-Amino-4-methyl-pentanoylamino)-4,5-dimethyl-octanoic acid; and
3-(2S-Amino-4-methyl-pentanoylamino)-4,5-dimethyl-nonanoic acid.

3. A compound selected from the group consisting of the following compounds and their pharmaceutically acceptable salts:

3S-[(2S-Amino-4-methyl-pentanoylamino)-methyl]-5R-methyl-octanoic acid;
3S-[(2S-Amino-4-methyl-pentanoylamino)-methyl]-5R-methyl-heptanoic acid;
3S-[(2S-Amino-4-methyl-pentanoylamino)-methyl]-5R-methyl-nonanoic acid;
3R-[(2S-Amino-4-methyl-pentanoylamino)-methyl]-4R,5R-dimethyl-heptanoic acid;
3R-[(2S-Amino-4-methyl-pentanoylamino)-methyl]-4R,5R-dimethyl-octanoic acid;
3R-[(2S-Amino-4-methyl-pentanoylamino)-methyl]-4R,5R-dimethyl-nonanoic acid;
3S-[(2S-Amino-4-methyl-pentanoylamino)-methyl]-5R-methyl-hexanoic acid;
3R-[(2S-Amino-4-methyl-pentanoylamino)-methyl]-4R,5R-dimethyl-hexanoic acid;
3S-[(2S-Amino-3-methyl-pentanoylamino)-methyl]-5R-methyl-heptanoic acid;
3S-[(2S-Amino-3-methyl-pentanoylamino)-methyl]-5R-methyl-octanoic acid;
3S-[(2S-Amino-3-methyl-pentanoylamino)-methyl]-5R-methyl-nonanoic acid;
3R-[(2S-Amino-3-methyl-pentanoylamino)-methyl]-4R,5R-dimethyl-heptanoic acid;
3R-[(2S-Amino-3-methyl-pentanoylamino)-methyl]-4R,5R-dimethyl-octanoic acid;
3R-[(2S-Amino-3-methyl-pentanoylamino)-methyl]-4R,R5-dimethyl-nonanoic acid;
3S-[(2S-Amino-3-methyl-pentanoylamino)-methyl]-5R-methyl-hexanoic acid;
3R-[(2S-Amino-3-methyl-pentanoylamino)-methyl]-4R,5R-dimethyl-hexanoic acid;
3S-[(2S-Amino-3-methyl-butyrylamino)-methyl]-5R-methyl-heptanoic acid;
3S-[(2S-Amino-3-methyl-butyrylamino)-methyl]-5R-methyl-octanoic acid
3S-[(2S-Amino-3-methyl-butyrylamino)-methyl]-5R-methyl-nonanoic acid;
3R-[(2S-Amino-3-methyl-butyrylamino)-methyl]-4R,5R-dimethyl-heptanoic acid;
3R-[(2S-Amino-3-methyl-butyrylamino)-methyl]-4R,5R-dimethyl-octanoic acid;
3R-[(2S-Amino-3-methyl-butyrylamino)-methyl]-4R,5R-dimethyl-nonanoic acid;
3S-[(2S-Amino-3-methyl-butyrylamino)-methyl]-5R-methyl-hexanoic acid;
3R-[(2S-Amino-3-methyl-butyrylamino)-methyl]-4R,5R-dimethyl-hexanoic acid;
3S-[(2S-Amino-propionylamino)-methyl]-5R-methyl-heptanoic acid;
3S-[(2S-Amino-propionylamino)-methyl]-5R-methyl-octanoic acid;
3S-[(2S-Amino-propionylamino)-methyl]-5R-methyl-nonanoic acid;
3R-[(2S-Amino-propionylamino)-methyl]-4R,5R-dimethyl-heptanoic acid;
3R-[(2S-Amino-propionylamino)-methyl]-4R,5R-dimethyl-octanoic acid;
3R-[(2S-Amino-propionylamino)-methyl]-4R,5R-dimethyl-nonanoic acid;
3S-[(2S-Amino-propionylamino)-methyl]-5R-methyl-hexanoic acid;
3R-[(2S-Amino-propionylamino)-methyl]-4R,5R-dimethyl-hexanoic acid;
3S-[(2S-Amino-acetylamino)-methyl]-5R-methyl-heptanoic acid;
3S-[(2S-Amino-acetylamino)-methyl]-5R-methyl-octanoic acid;
3S-[(2S-Amino-acetylamino)-methyl]-5R-methyl-heptanoic acid;
3R-[(2S-Amino-acetylamino)-methyl]-4R,5R-dimethyl-heptanoic acid;
3R-[(2S-Amino-acetylamino)-methyl]-4R,5R-dimethyl-octanoic acid;
3R-[(2S-Amino-acetylamino)-methyl]-4R,5R-dimethyl-nonanoic acid;
3S-[(2S-Amino-acetylamino)-methyl]-5R-methyl-hexanoic acid;
3R-[(2S-Amino-acetylamino)-methyl]-4R,5R-dimethyl-hexanoic acid;
3S-(2S-Amino-acetylamino)-5R-methyl-heptanoic acid;
3S-(2S-Amino-acetylamino)-5R-methyl-octanoic acid;
3S-(2S-Amino-acetylamino)-5R-methyl-nonanoic acid;
3R-(2S-Amino-acetylamino)-4R,5R-dimethyl-heptanoic acid;
3R-(2S-Amino-acetylamino)-4R,5R-dimethyl-octanoic acid;
3R-(2S-Amino-acetylamino)-4R,5R-dimethyl-nonanoic acid;
3R-(2S-Amino-propionylamino)-5R-methyl-heptanoic acid;

3S-(2S-Amino-propionylamino)-5R-methyl-octanoic acid;
3S-(2S-Amino-propionylamino)-5R-methyl-nonanoic acid;
3R-(2S-Amino-propionylamino)-4R,5R-dimethyl-heptanoic acid;
3R-(2S-Amino-propionylamino)-4R,5R-dimethyl-octanoic acid;
3R-(2S-Amino-propionylamino)-4R,5R-dimethyl-nonanoic acid;
3S-(2S-Amino-3-methyl-butyrylamino)-5R-methyl-heptanoic acid;
3S-(2S-Amino-3-methyl-butyrylamino)-5R-methyl-octanoic acid;
3S-(2S-Amino-3-methyl-butyrylamino)-5R-methyl-nonanoic acid;
3R-(2S-Amino-3-methyl-butyrylamino)-4R,5R-dimethyl-heptanoic acid;
3R-(2S-Amino-3-methyl-butyrylamino)-4R,5R-dimethyl-octanoic acid;
3R-(2S-Amino-3-methyl-butyrylamino)-4R,5R-dimethyl-nonanoic acid;
3S-(2S-Amino-3-methyl-pentanoylamino)-5R-methyl-heptanoic acid;
3S-(2S-Amino-3-methyl-pentanoylamino)-5R-methyl-octanoic acid;
3S-(2S-Amino-3-methyl-pentanoylamino)-5R-methyl-nonanoic acid;
3R-(2S-Amino-3-methyl-pentanoylamino)-4R,5R-dimethyl-heptanoic acid;
3R-(2S-Amino-3-methyl-pentanoylamino)-4R,5R-dimethyl-octanoic acid;
3R-(2S-Amino-3-methyl-pentanoylamino)-4R,5R-dimethyl-nonanoic acid;
3S-(2S-Amino-4-methyl-pentanoylamino)-5R-methyl-heptanoic acid;
3S-(2S-Amino-4-methyl-pentanoylamino)-5R-methyl-octanoic acid;
3S-(2S-Amino-4-methyl-pentanoylamino)-5R-methyl-nonanoic acid;
3R-(2S-Amino-4-methyl-pentanoylamino)-4R,5R-dimethyl-heptanoic acid;
3R-(2S-Amino-4-methyl-pentanoylamino)-4R,5R-dimethyl-octanoic acid; and
3R-(2S-Amino-4-methyl-pentanoylamino)-4R,5R-dimethyl-nonanoic acid.

4. A compound having the formula IV

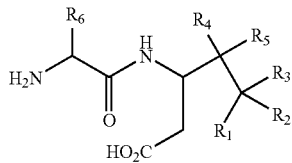

IV wherein $R_1$ is hydrogen or $(C_1-C_{10})$alkyl optionally substituted with from one to five fluorine atoms;
$R_2$ is hydrogen or $(C_1-C_6)$alkyl;
$R_1$ and $R_2$, together with the carbon to which they are attached, may form a three to six membered cycloalkyl ring;
$R_3$ is selected from the group consisiting of hydrogen, $(C_1-C_8)$alkyl, $(C_3-C_6)$cycloalkyl, $(C_3-C_6)$cycloalkyl-$(C_1-C_6)$alkyl, phenyl, phenyl-$(C_1-C_3)$alkyl, pyridyl, and pyridyl-$(C_1-C_3)$alkyl, wherein each of the foregoing alkyl moieties can be optionally substituted with from one to five fluorine atoms, preferably with from zero to three fluorine atoms, and wherein said phenyl and said pyridyl and the phenyl and pyridyl moieties of said phenyl-$(C_1-C_3)$alkyl and said pyridyl-$(C_1-C_3)$alkyl, respectively, can be optionally substituted with from one to three substituents, independently selected from chloro, fluoro, amino, nitro, cyano, $(C_1-C_3)$alkylamino, $(C_1-C_3)$alkyl optionally substituted with from one to three fluorine atoms and $(C_1-C_3)$alkoxy optionally substituted with from one to three fluorine atoms;
$R_4$ is hydrogen or $(C_1-C_6)$alkyl optionally substituted with from one to five fluorine atoms;
$R_5$ is hydrogen or $(C_1-C_6)$alkyl optionally substituted with from one to five fluorine atoms;
$R_4$ and $R_5$, together with the carbon to which they are attached, may form a three to six membered cycloalkyl ring; and
$R_6$ is a side chain derived from an α-amino acid or other $(C_1-C_8)$alkyl;
or a pharmaceutically acceptable salt of such a compound.

5. A compound according to claim 4 selected from the group consisting of the following compounds and their pharmaceutically acceptable salts:
3-(2-Amino-acetylamino)-5-methyl-heptanoic acid;
3-(2-Amino-acetylamino)-5-methyl-octanoic acid;
3-(2-Amino-acetylamino)-5-methyl-nonanoic acid;
3-(2-Amino-acetylamino)-4,5-dimethyl-heptanoic acid;
3-(2-Amino-acetylamino)-4,5-dimethyl-octanoic acid;
3-(2-Amino-acetylamino)-4,5-dimethyl-nonanoic acid;
3-(2-Amino-propionylamino)-5-methyl-heptanoic acid;
3-(2-Amino-propionylamino)-5-methyl-octanoic acid;
3-(2-Amino-propionylamino)-5-methyl-nonanoic acid;
3-(2-Amino-propionylamino)-4,5-dimethyl-heptanoic acid;
3-(2-Amino-propionylamino)-4,5-dimethyl-octanoic acid;
3-(2-Amino-propionylamino)-4,5-dimethyl-nonanoic acid;
3-(2-Amino-3-methyl-butyrylamino)-5-methyl-heptanoic acid;
3-(2-Amino-3-methyl-butyrylamino)-5-methyl-octanoic acid;
3-(2-Amino-3-methyl-butyrylamino)-5-methyl-nonanoic acid;
3-(2-Amino-3-methyl-butyrylamino)-4,5-dimethyl-heptanoic acid;
3-(2-Amino-3-methyl-butyrylamino)-4,5-dimethyl-octanoic acid;
3-(2-Amino-3-methyl-butyrylamino)-4,5-dimethyl-nonanoic acid;
3-(2-Amino-3-methyl-pentanoylamino)-5-methyl-heptanoic acid;
3-(2-Amino-3-methyl-pentanoylamino)-5-methyl-octanoic acid;
3-(2-Amino-3-methyl-pentanoylamino)-5-methyl-nonanoic acid;
3-(2-Amino-3-methyl-pentanoylamino)-4,5-dimethyl-heptanoic acid;
3-(2-Amino-3-methyl-pentanoylamino)-4,5-dimethyl-octanoic acid;
3-(2-Amino-3-methyl-pentanoylamino)-4,5-dimethyl-nonanoic acid;
3-(2-Amino-4-methyl-pentanoylamino)-5-methyl-heptanoic acid;

3-(2-Amino-4-methyl-pentanoylamino)-5-methyl-octanoic acid;
3-(2-Amino-4-methyl-pentanoylamino)-5-methyl-nonanoic acid;
3-(2-Amino-4-methyl-pentanoylamino)-4,5-dimethyl-heptanoic acid;
3-(2-Amino-4-methyl-pentanoylamino)-4,5-dimethyl-octanoic acid; and
3-(2-Amino-4-methyl-pentanoylamino)-4,5-dimethyl-nonanoic acid.

6. A compound having the formula V

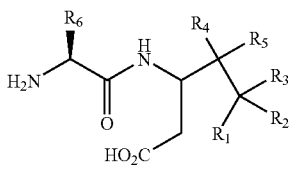

wherein $R_1$ is hydrogen or $(C_1-C_{10})$alkyl optionally substituted with from one to five fluorine atoms;

$R_2$ is hydrogen or $(C_1-C_6)$alkyl;

$R_1$ and $R_2$, together with the carbon to which they are attached, may form a three to six membered cycloalkyl ring;

$R_3$ is selected from the group consisting of hydrogen, $(C_1-C_8)$alkyl, $(C_3-C_6)$cycloalkyl, $(C_3-C_6)$cycloalkyl-$(C_1-C_6)$alkyl, phenyl, phenyl-$(C_1-C_3)$alkyl, pyridyl, and pyridyl-$(C_1-C_3)$alkyl, wherein each of the foregoing alkyl moieties can be optionally substituted with from one to five fluorine atoms, preferably with from zero to three fluorine atoms, and wherein said phenyl and said pyridyl and the phenyl and pyridyl moieties of said phenyl-$(C_1-C_3)$alkyl and said pyridyl-$(C_1-C_3)$alkyl, respectively, can be optionally substituted with from one to three substituents, preferably with from zero to two substituents, independently selected from chloro, fluoro, amino, nitro, cyano, $(C_1-C_3)$alkylamino, $(C_1-C_3)$alkyl optionally substituted with from one to three fluorine atoms and $(C_1-C_3)$alkoxy optionally substituted with from one to three fluorine atoms;

$R_4$ is hydrogen or $(C_1-C_6)$alkyl optionally substituted with from one to five fluorine atoms;

$R_5$ is hydrogen or $(C_1-C_6)$alkyl optionally substituted with from one to five fluorine atoms;

$R_4$ and $R_5$, together with the carbon to which they are attached, may form a three to six membered cycloalkyl ring; and $R_6$ is a side chain derived from an α-amino acid or other $(C_1-C_8)$alkyl;

or a pharmaceutically acceptable salt of such a compound.

7. A compound according to claim 6 selected from the group consisting of the following compounds and their pharmaceutically acceptable salts:

3-(2S-Amino-acetylamino)-5-methyl-heptanoic acid;
3-(2S-Amino-acetylamino)-5-methyl-octanoic acid;
3-(2S-Amino-acetylamino)-5-methyl-nonanoic acid;
3-(2S-Amino-acetylamino)-4,5-dimethyl-heptanoic acid;
3-(2S-Amino-acetylamino)-4,5-dimethyl-octanoic acid;
3-(2S-Amino-acetylamino)-4,5-dimethyl-nonanoic acid;
3-(2S-Amino-propionylamino)-5-methyl-heptanoic acid;
3-(2S-Amino-propionylamino)-5-methyl-octanoic acid;
3-(2S-Amino-propionylamino)-5-methyl-nonanoic acid;
3-(2S-Amino-propionylamino)-4,5-dimethyl-heptanoic acid;
3-(2S-Amino-propionylamino)-4,5-dimethyl-octanoic acid;
3-(2S-Amino-propionylamino)-4,5-dimethyl-nonanoic acid;
3-(2S-Amino-3-methyl-butyrylamino)-5-methyl-heptanoic acid;
3-(2S-Amino-3-methyl-butyrylamino)-5-methyl-octanoic acid;
3-(2S-Amino-3-methyl-butyrylamino)-5-methyl-nonanoic acid;
3-(2S-Amino-3-methyl-butyrylamino)-4,5-dimethyl-heptanoic acid;
3-(2S-Amino-3-methyl-butyrylamino)-4,5-dimethyl-octanoic acid;
3-(2S-Amino-3-methyl-butyrylamino)-4,5-dimethyl-nonanoic acid;
3-(2S-Amino-3-methyl-pentanoylamino)-5-methyl-heptanoic acid;
3-(2S-Amino-3-methyl-pentanoylamino)-5-methyl-octanoic acid;
3-(2S-Amino-3-methyl-pentanoylamino)-5-methyl-nonanoic acid;
3-(2S-Amino-3-methyl-pentanoylamino)-4,5-dimethyl-heptanoic acid;
3-(2S-Amino-3-methyl-pentanoylamino)-4,5-dimethyl-octanoic acid;
3-(2S-Amino-3-methyl-pentanoylamino)-4,5-dimethyl-nonanoic acid;
3-(2S-Amino-4-methyl-pentanoylamino)-5-methyl-heptanoic acid;
3-(2S-Amino-4-methyl-pentanoylamino)-5-methyl-octanoic acid;
3-(2S-Amino-4-methyl-pentanoylamino)-5-methyl-nonanoic acid;
3-(2S-Amino-4-methyl-pentanoylamino)-4,5-dimethyl-heptanoic acid;
3-(2S-Amino-4-methyl-pentanoylamino)-4,5-dimethyl-octanoic acid; and
3-(2S-Amino-4-methyl-pentanoylamino)-4,5-dimethyl-nonanoic acid.

8. A compound having the formula VI

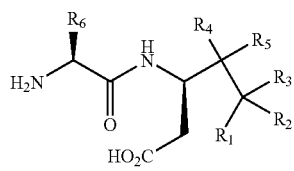

wherein $R_1$ is hydrogen or $(C_1-C_{10})$alkyl optionally substituted with from one to five fluorine atoms;

$R_2$ is hydrogen or $(C_1-C_6)$alkyl;

$R_1$ and $R_2$, together with the carbon to which they are attached, may form a three to six membered cycloalkyl ring;

$R_3$ is selected from the group consisting of hydrogen, $(C_1-C_8)$alkyl, $(C_3-C_6)$cycloalkyl, $(C_3-C_6)$cycloalkyl-$(C_1-C_6)$alkyl, phenyl, phenyl-$(C_1-C_3)$alkyl, pyridyl, and pyridyl-$(C_1-C_3)$alkyl, wherein each of the foregoing alkyl moieties can be optionally substituted with from one to five fluorine atoms, preferably with from zero to three fluorine atoms, and wherein said phenyl and said pyridyl and the phenyl and pyridyl moieties of said phenyl-$(C_1-C_3)$alkyl and said pyridyl-$(C_1-C_3)$alkyl, respectively, can be optionally substituted with from one to three substituents, preferably with from zero to two substituents, independently selected from chloro, fluoro, amino, nitro, cyano, $(C_1-C_3)$alkylamino, $(C_1-C_3)$alkyl optionally substituted with from one to three fluorine atoms;

$R_4$ is hydrogen or $(C_1-C_6)$alkyl optionally substituted with from one to five fluorine atoms;

$R_5$ is hydrogen or $(C_1-C_6)$alkyl optionally substituted with from one to five fluorine atoms;

$R_4$ and $R_5$, together with the carbon to which they are attached, may form a three to six membered cycloalkyl ring; and $R_6$ is a side chain derived from an α-amino acid or other $(C_1-C_8)$alkyl;

or a pharmaceutically acceptable salt of such a compound.

9. A compound according to claim 8 selected from the group consisting of the following compounds and their pharmaceutically acceptable salts:

3-(2S-Amino-acetylamino)-5-methyl-heptanoic acid;
3S-(2S-Amino-acetylamino)-5-methyl-octanoic acid;
3S-(2S-Amino-acetylamino)-5-methyl-nonanoic acid;
3R-(2S-Amino-acetylamino)-4,5-dimethyl-heptanoic acid;
3R-(2S-Amino-acetylamino)-4,5-dimethyl-octanoic acid;
3R-(2S-Amino-acetylamino)-4,5-dimethyl-nonanoic acid;
3S-(2S-Amino-propionylamino)-5-methyl-heptanoic acid;
3S-(2S-Amino-propionylamino)-5-methyl-octanoic acid;
3S-(2S-Amino-propionylamino)-5-methyl-nonanoic acid;
3R-(2S-Amino-propionylamino)-4,5-dimethyl-heptanoic acid;
3R-(2S-Amino-propionylamino)-4,5-dimethyl-octanoic acid;
3R-(2S-Amino-propionylamino)-4,5-dimethyl-nonanoic acid;
3S-(2S-Amino-3-methyl-butyrylamino)-5-methyl-heptanoic acid;
3S-(2S-Amino-3-methyl-butyrylamino)-5-methyl-octanoic acid;
3S-(2S-Amino-3-methyl-butyrylamino)-5-methyl-nonanoic acid;
3R-(2S-Amino-3-methyl-butyrylamino)-4,5-dimethyl-heptanoic acid;
3R-(2S-Amino-3-methyl-butyrylamino)-4,5-dimethyl-octanoic acid;
3R-(2S-Amino-3-methyl-butyrylamino)-4,5-dimethyl-nonanoic acid;
3S-(2S-Amino-3-methyl-pentanoylamino)-5-methyl-heptanoic acid;
3S-(2S-Amino-3-methyl-pentanoylamino)-5-methyl-octanoic acid;
3S-(2S-Amino-3-methyl-pentanoylamino)-5-methyl-nonanoic acid;
3R-(2S-Amino-3-methyl-pentanoylamino)-4,5-dimethyl-heptanoic acid;
3R-(2S-Amino-3-methyl-pentanoylamino)-4,5-dimethyl-octanoic acid;
3R-(2S-Amino-3-methyl-pentanoylamino)-4,5-dimethyl-nonanoic acid;
3S-(2S-Amino-4-methyl-pentanoylamino)-5-methyl-heptanoic acid;
3S-(2S-Amino-4-methyl-pentanoylamino)-5-methyl-octanoic acid;
3S-(2S-Amino-4-methyl-pentanoylamino)-5-methyl-nonanoic acid;
3R-(2S-Amino-4-methyl-pentanoylamino)-4,5-dimethyl-heptanoic acid;
3R-(2S-Amino-4-methyl-pentanoylamino)-4,5-dimethyl-octanoic acid; and
3R-(2S-Amino-4-methyl-pentanoylamino)-4,5-dimethyl-nonanoic acid.

10. A compound having the formula VII

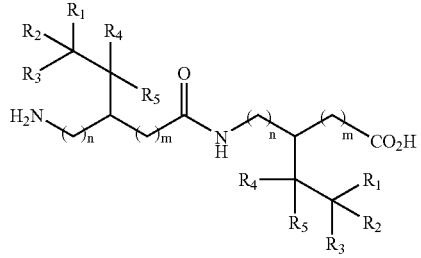

VII wherein $R_1$ is hydrogen or $(C_1-C_{10})$alkyl optionally substituted with from one to five fluorine atoms;

$R_2$ is hydrogen or $(C_1-C_6)$alkyl;

$R_1$ and $R_2$, together with the carbon to which they are attached, may form a three to six membered cycloalkyl ring;

$R_3$ is selected from the group consisting of hydrogen, $(C_1-C_8)$alkyl, $(C_3-C_6)$cycloalkyl, $(C_3-C_6)$cycloalkyl-$(C_1-C_6)$alkyl, phenyl, phenyl-$(C_1-C_3)$alkyl, pyridyl, and pyridyl-$(C_1-C_3)$alkyl, wherein each of the foregoing alkyl moieties can be optionally substituted with from one to five fluorine atoms, preferably with from zero to three fluorine atoms, and wherein said phenyl and said pyridyl and the phenyl and pyridyl moieties of said phenyl-$(C_1-C_3)$alkyl and said pyridyl-$(C_1-C_3)$alkyl, respectively, can be optionally substituted with from one to three substituents, independently selected from chloro, fluoro, amino, nitro, cyano, $(C_1-C_3)$alkylamino, $(C_1-C_3)$alkyl optionally substituted with from one to three fluorine atoms and $(C_1-C_3)$alkoxy optionally substituted with from one to three fluorine atoms;

$R_4$ is hydrogen or $(C_1-C_6)$alkyl optionally substituted with from one to five fluorine atoms;

$R_5$ is hydrogen or $(C_1-C_6)$alkyl optionally substituted with from one to five fluorine atoms;

$R_4$ and $R_5$, together with the carbon to which they are attached, may form a three to six membered cycloalkyl ring; and $R_1$-$R_5$ and m and n can be the same or different at each occurrence;

or a pharmaceutically acceptable salt of such a compound.

11. A compound according to claim 10 selected from the group consisting of the following compounds and their pharmaceutically acceptable salts:

3-(3-Amino-5-methyl-heptanoylamino)-5-methyl-heptanoic acid;
3-(3-Amino-5-methyl-octanoylamino)-5-methyl-octanoic acid; and
3-(3-Amino-5-methyl-nonanoylamino)-5-methyl-nonanoic acid.

12. A pharmaceutical composition comprising a therapeutically effective amount of a compound according to any of claims 1 to 11, or a pharmaceutically acceptable salt thereof, and a pharmaceutically acceptable carrier.

* * * * *